US005726302A

United States Patent [19]
Ugarkar et al.

[11] Patent Number: 5,726,302
[45] Date of Patent: Mar. 10, 1998

[54] WATER SOLUBLE ADENOSINE KINASE INHIBITORS

[75] Inventors: Bheemarao G. Ugarkar, Escondido; Mark D. Erion, Del Mar; Jorge E. Gomez Galeno, La Jolla, all of Calif.

[73] Assignee: Gensia Inc., San Diego, Calif.

[21] Appl. No.: 473,492

[22] Filed: Jun. 7, 1995

Related U.S. Application Data

[63] Continuation-in-part of Ser. No. 812,916, Dec. 23, 1991, abandoned, which is a continuation-in-part of Ser. No. 647,117, Jan. 23, 1991, abandoned, which is a continuation-in-part of Ser. No. 466,979, Jan. 18, 1990, abandoned, which is a continuation-in-part of Ser. No. 408,707, Sep. 18, 1989, abandoned.

[51] Int. Cl.$^6$ .................................................... C07H 19/16
[52] U.S. Cl. .................. 536/27.13; 536/27.2; 536/27.6; 536/27.61; 536/27.62; 536/27.63; 536/27.7
[58] Field of Search .............................. 536/27.13, 27.2, 536/27.6, 27.61, 27.62, 27.63, 27.7; 514/45, 46

[56] References Cited

U.S. PATENT DOCUMENTS 4,904,666   2/1990   Friebe et al. .

FOREIGN PATENT DOCUMENTS

| 0 496 617 A | 7/1992 | European Pat. Off. . |
| WO 94/17803 | 8/1994 | WIPO . |
| WO 94/18215 | 8/1994 | WIPO . |

OTHER PUBLICATIONS

Abdalla, G.M. and Sowell, J.W., Sr., *J. Heterocyclic Chem.* 24, 297–301 (1987).
Achtenberg et al., *Biochem. J.*, 235, 13–17 (1986).
Agarwal, K.C., et al. *Biochem. Pharmacol.*, 28, 501–10 (1978).
Amarnath, V. and Madhav, R., *Synth.* 837, 846–51 (Dec. 1974).
Bergrstrom, D.E., et al., *J. Med. Chem.*, 27, 285–92 (1984).
Bontemps et al., *Proc. Natl. Acad. Sci. USA*, 80, 2829–33 (1983).
Caldwell and Henderson, *Cancer Chemother. Rep.*, 2, 237–46 (1971).
Carboni, R.A., et al., *J. Am. Chem. Soc.*, 80, 2838–40 (1958).
Chat, I., et al., *J. Med. Chem.*, 18, 161–65 (1975).
Cottam, H.B., et al., *J. Med. Chem.*, 27, 119–27 (1984).
Davies et al., *Biochem. Pharmacol.*, 35, 3021–29 (1986).
Davies et al., *Biochem. Pharmacol.*, 33, 347–55 (1984).
Davoll, J., *J. Chem. Soc.*, 131–38 (1960).
Divekar, A.Y. and Hakala, M.T., *Mol. Pharmacol.*, 7, 663–73 (1971).
Firestein et al., *J. Immunology* 154, 326–34 (1995).
Gewald, R., Z. *Chem.* 1, 349 (1961).
Green, *J. Supramol. Structure*, 13:175–182 (1980).
Henderson et al., *Cancer Chemotherapy Rep.* Part 2, 3, 71–85 (1972).
Hinshaw, B.C., et al., *J. Heterocyclic Chem.*, 6, 215–21 (1969).
Ikehara, M., et al., *Tetrahedron*, 26, 5757–63 (1970).
Keil et al., *Life Sciences* 5, 171–76 (1992).
Kobayashi, S., *Chem. Pharm. Bull.*, 21, 941–51 (1973).
Newby et al., *Biochem. J.*, 214, 317–323 (1983).
Noell, C.W., et al., *J. Heterocyclic Chem.*, 1, 34–41 (1964).
Miller et al., *J. Biol. Chem.*, 254, 2346–52 (1979).
Pak, et al., *Soc. for Neuroscience Abs.*, 20, 149.2 (1994).
Phillis et al., *Life Sciences*, 53, 497–502 (1993).
Prescott et al., *Nucleosides & Nucleotide*, 8, 297 (1989).
Pudlo, J.S., et al., *J. Med. Chem.*, 33, 1984–92 (1990).
Rosemeyer, H. and Seela, F., *Helv. Chim. Acta*, 71, 1573–85 (1988).
Schrader, in *Regulatory Function of Adenosiner*; Berne et al., eds. pp. 133–156 (1983).
Sciotti et al., *J. Cerebral Blood Flow Metab.*, 13, 201–207 (1993).
Seela, F., et al., *Liebigs Ann. Chem.*, 15–19 (1987).
Stout, M.G., et al., *J. Org. Chem.*, 33, 1219–25 (1968).
Synder, J.R. et al., *Carbohydrate Res.*, 163, 169–88 (1987).
Taylor, E.C. and Hendess, R.W., *J. Am. Chem. Soc.*, 87, 1995–2003 (1965).
Taylor, E.C., et al., *J. Org. Chem.*, 31, 342–43 (1966).
Tominaga, Y., et al., *J. Heterocyclic Chem.*, 27, 647–60 (1990).
White, *Soc. Neurosci. Abs.*, 20, 308.9 (1994).
Wu, et al., *Cytobios*, 50, 7–12 (1987).
Zhang et al., *J. Pharmacol. Exper. Ther.* 264(3), 1415 (1993).
Zoref-Shani et al., *J. Mol. Cell. Cardiol.*, 20, 23–33 (1988).

*Primary Examiner*—James O. Wilson
*Attorney, Agent, or Firm*—Darby & Darby

[57] ABSTRACT

This invention relates to adenosine kinase inhibitors and to nucleoside analogs, specifically to water soluble, aryl substituted 4-amino pyrrolo[2,3-d] pyrimidine and pyrazolo[3,4-d] pyrimidine nucleoside analogs having activity as adenosine kinase inhibitors. The invention also relates to the preparation and use of these adenosine kinase inhibitors in the treatment of cardiovascular, and cerebrovascular diseases, inflammation and other diseases which can be regulated by increasing the local concentration of adenosine.

43 Claims, No Drawings

WATER SOLUBLE ADENOSINE KINASE INHIBITORS

CROSS REFERENCES TO RELATED APPLICATIONS

This application is a continuation in part of Ser. No. 07/812,916, filed Dec. 23, 1991, now abandoned, which is a continuation in part of Ser. No. 07/647,117, filed Jan. 23, 1991, now abandoned, which is a continuation in part of Ser. No. 07/466,979, filed Jan. 18, 1990, now abandoned, which is a continuation in part of Ser. No. 07/408,707, filed Sep. 18, 1989, now abandoned. The disclosures of these applications are incorporated herein by reference.

This invention relates to adenosine kinase inhibitors and to nucleoside analogs, specifically to water soluble, aryl substituted 4-amino pyrrolo[2,3-d] pyrimidine and pyrazolo [3,4-d] pyrimidine nucleoside analogs having activity as adenosine kinase inhibitors. The invention also relates to the preparation and use of these adenosine kinase inhibitors in the treatment of cardiovascular and cerebrovascular diseases, inflammation and other diseases which can be regulated by increasing the local concentration of adenosine.

BACKGROUND OF THE INVENTION

Adenosine is an endogenously produced molecule that plays a major role in a variety of important cellular processes.. It is a vasodilator, can inhibit immune function, enhance activation of mast cells (associated with allergic reactions), inhibit neutrophil oxygen free-radical production, is antiarrhythmic, and is an inhibitory neurotransmitter. Adenosine is phosphorylated to adenosine triphosphate (ATP) which is used by all cells to store energy for use in future energy-utilizing metabolic reactions or mechanical work (e.g. muscle contraction). Extracellular adenosine, frequently produced by breakdown of intracellular ATP pools, evokes a variety of pharmacological responses through activation of extracellular adenosine receptors located on the surface of nearly all cells. For example, adenosine produces a variety of cardiovascular related effects including vasodilation, inhibition of platelet aggregation, and negative inotropic, chronotropic and dromotropic effects on the heart. Adenosine also has effects within the central nervous system (CNS) including inhibition of neurotransmitter release from presynaptic neurons and inhibition of post-synaptic neuron firing in brain and the spinal cord and at sites of inflammation, such as inhibition of neutrophil adhesion to endothelial cells and inhibition of neutrophil oxygen free-radical production.

Compounds that increase extracellular adenosine can be beneficial to living organisms, particularly under certain conditions. For example, compounds that increase adenosine levels have been associated with the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

Adenosine kinase is a cytostolic enzyme which catalyzes the phosphorylation of adenosine to AMP. Inhibition of adenosine kinase can potentially reduce the ability of the cell to utilize adenosine, leading to increased adenosine outside of the cell where it is pharmacologically active. However, the regulation of adenosine concentration is complex and involves other adenosine-metabolizing enzymes each with different kinetic properties and mechanisms of regulation. Adenosine can also be deaminated to inosine by adenosine deaminase (ADA) and condensed with L-homocysteine to S-adenosylhomocysteine (SAH) by SAH hydrolase. The role of each of these enzymes in modulating adenosine concentration is dependent on the prevailing physiological conditions, is tissue specific and is not well understood.

A number of nucleosides including pyrrolo[2,3-d] pyrimidine and pyrazolo[3,4-d]pyrimidine analogs have been evaluated for inhibition of adenosine kinase but were reported to have $K_i$'s of greater than 800 nM. Caldwell and Henderson, Cancer Chemother. Rep., 2:237–46 (1971); Miller et al., J. Biol. Chem., 254:2346–52 (1979). A few compounds have been reported as potent inhibitors of adenosine kinase with $K_i$'s of less than 100 nM. These are the purine nucleosides, 5'-amino-5'-deoxyadenosine (Miller et al.) and 1,12-bis(adenosin-$N^6$-yl)dodecane (Prescott et al., Nucleosides & Nucleotides, 8:297 (1989)); and the pyrrolopyrimidine nucleosides, 5-iodotubercidin (Henderson et al., Cancer Chemotherapy Rep. Part 2, 3:71–85 (1972); Bontemps et al., Proc. Natl. Acad. Sci. USA, 80:2829–33 (1983); Davies et al., Biochem. Pharmacol., 35:3021–29 (1986)) and 5'-deoxy-5-iodotubercidin (Davies et al., Biochem. Pharmacol., 33:347–55 (1984) and 35:3021–29 (1986)).

Some of these compounds have been used to evaluate whether adenosine kinase inhibition might lead to increased extracellular adenosine concentrations. In rat cardiomyocytes, inhibition of adenosine deaminase by 2'-deoxycoformycin was reported to have no effect on adenosine release from the cells. In contrast, inhibition of ADA together with adenosine kinase by 5'-amino-5'-deoxyadenosine resulted in a 6-fold increase in adenosine release. Zoref-Shani et al., J. Mol. Cell. Cardiol., 20:23–33 (1988). The effects of the adenosine kinase inhibitor alone were not reported. Similar results were reported in isolated guinea pig hearts; in these studies addition of 5'-amino-5'-deoxyadenosine to the perfusion medium, in the presence of EHNA to inhibit deamination, was reported to result in a 15-fold increase of adenosine release. Schrader in Regulatory Function of Adenosine; (Berne et al.) eds. pp. 133–156 (1983). These effects were not apparent in the absence of ADA inhibition, and other studies using isolated rat hearts perfused with 5-iodotubercidin alone, have reported no increase in perfusate adenosine concentration under normoxic conditions Newby et al., Biochem. J., 214:317–323 (1983), or under hypoxic, anoxic or ischemic conditions, Achtenberg et al., Biochem. J., 235:13–17 (1986). In other studies, adenosine release has been measured in neuroblastoma cells in culture and compared with that of a variant deficient in adenosine kinase (AK$^-$). The AK cells used in this study were said to release adenosine at an accelerated rate; the concentration of adenosine in the growth medium was reported to be elevated compared to the normal cells. Green, J. Supramol. Structure, 13:175–182 (1980). In rat and guinea pig brain slices, adenosine uptake was reportedly inhibited by the adenosine kinase inhibitors, 5-iodotubercidin and 5'-deoxy-5-iodotubercidin. Davis et al., Biochem. Pharmacol., 33:347–55 (1984). However, inhibition of uptake and intracellular trapping via phosphorylation does not necessarily result in increased extracellular adenosine, since the adenosine could enter other metabolic pathways or the percentage of adenosine being phosphorylated could be insignificant compared to the total adenosine removed.

The effects of adenosine and certain inhibitors of adenosine catabolism, including 5-iodotubericidin were evaluated in an experimental model in which dog hearts were subjected to ischemia and reperfusion; 5-iodotubericidin was reported to have inconsistent effects. Wu. et al., *Cytobios*, 50:7–12 (1987).

Although the adenosine kinase inhibitors, 5'-amino-5'-deoxyadenosine and 5-iodotubercidin have been widely used in experimental models, the susceptibility of 5'-amino-5'-deoxyadenosine to deamination, and hence its potentially short half life, and the cytotoxicity of 5-iodotubercidin make their clinical utility limited and may limit interpretations based on these compounds. The known pyrrolo[2,3-d]pyrimidines, 5-iodotubercidin and 5'-deoxy-5-iodotubercidin have been reported to cause pronounced general flaccidity and much-reduced spontaneous locomotor activity in mice, interpreted to be skeletal muscle relaxation; to cause hypothermia in mice; and to decrease blood pressure and heart rate in anesthetized rats. Daves et al., *Biochem. Pharmacol.*, 33:347–55 (1984) and 35:3021–29 (1986); and U.S. Pat. No. 4,455,420). The skeletal muscle effects of these compounds have been poorly documented, while the other effects were considered significant toxicities.

More recent references concerned with the mechanisms and effects of adenosine kinase inhibitors are Keil et al., *Life Sciences* 51:171–76 (1992); Zhang et al., *J.Pharmacol. Exper. Ther.* 264(3): 1415 (1993); Phillis et al., *Life Sciences*, 53:497–502 (1993); Sciotti et al., *J. Cerebral Blood Flow Metab.*, 13:201–207 (1993); Pak et al., *Soc. for Neuroscience Abs.*, 20:149.2 (1994); White, *Soc. Neurosci. Abs.*, 20:308.9 (1994); and Firestein et al., *J. Immunology* 154:326–34 (1995). These publications in general show that adenosine kinase inhibitors, as a class, have a role in brain functions, and show promise in connection with the treatment of neurological conditions such as seizures. One reference, Phillis et al., indicates that the known adenosine kinase inhibitor 5-iodotubercidin apparently does not protect against ischemic cerebral injury. Keil et al. disclose that adenosine kinase plays a key role in the mediation of nervous system responses to stimulus, particularly pain (antinociception), but notes that the control of endogenous adenosine concentrations by such means is a complex process requiring further study.

Thus, there is a need for selective, potent, and bioavailable adenosine kinase inhibitors with a useful half-life, i.e. compounds which can be exploited to beneficially influence or control endogenous adenosine kinase activity, and therefore, extracellular adenosine levels. The compounds of the invention are suitable adenosine kinase inhibitors having these characteristics.

SUMMARY OF THE INVENTION

The invention is directed to novel nucleoside analogs which comprise a ribofuranosyl or lyxofuranosyl linked to an aryl substituted 4-amino pyrrolo[2,3-d] pyrimidine or pyrazolo[3,4-d] pyrimidine nucleoside. Preferred compounds are 4-arylamino-5-aryl pyrrolo pyrimidines and 3-aryl-4-arylamino pyrazolo pyrimidines with at least one aryl further substituted with a group that enhances water solubility. Suitable water solubilizing groups include amino-containing alkyl groups, guanidino and amidino containing groups, or other groups containing a basic nitrogen.

It has been discovered that these compounds are advantageously water soluble, and are highly selective adenosine kinase inhibitors with potencies significantly higher than other known adenosine kinase inhibitors. The compounds are also nontoxic, particularly in connection with liver function.

The invention concerns the compounds themselves, the preparation of these compounds, and the in vitro and in vivo adenosine kinase inhibition activity of these compounds. Another aspect of the invention is directed to the clinical use of the compounds to increase adenosine concentrations in biological systems. For example, in vivo inhibition of adenosine kinase prevents phosphorylation of adenosine resulting in higher local concentrations of endogenous adenosine.

The compounds of the invention possess advantages for pharmaceutical use such as enhanced pharmacological selectivity, efficacy, bioavailability, ease of manufacture, compound stability and ease of formulation for intravenous administration.

The compounds of the invention may be used clinically to treat medical conditions where an increased localized adenosine concentration is beneficial. Accordingly, the invention is directed to the treatment of ischemic conditions such as stroke, as well as other conditions benefitted by enhanced adenosine levels, such as inflammation, arthritis, seizures, epilepsy and other neurological conditions. The compounds are also useful for treating pain, as muscle relaxants, and for inducing sleep.

The invention is also directed to prodrugs and pharmaceutically acceptable salts of the compounds described, and to pharmaceutical compositions suitable for different routes of drug administration and which comprise a therapeutically effective amount of a described compound admixed with a pharmacologically acceptable carrier.

Definitions

The following terms generally have the following meanings.

The term "aryl" refers to aromatic groups, which have at least one ring having a conjugated pi electron system, including for example carbocyclic aryl, heterocyclic aryl and biaryl groups, all of which may be optionally substituted. Carbocyclic aryl groups are groups wherein all the ring atoms on the aromatic ring are carbon atoms, such as phenyl. Also included are optionally substituted phenyl groups, being preferably phenyl or phenyl substituted by one to three substituents, preferably lower alkyl, hydroxy, lower alkoxy, lower alkanoyloxy, halogen, cyano, perhalo lower alkyl, lower acylamino, lower alkoxycarbonyl, amino, alkylamino, carboxamido, and sulfamido.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, pyrimidyl, pyrazinyl, imidazolyl, and the like, all optionally substituted.

Optionally substituted furanyl represents 2- or 3-furanyl or 2- or 3-furanyl preferably substituted by lower alkyl or halogen. Optionally substituted pyridyl represents 2-, 3- or 4-pyridyl or 2-, 3- or 4-pyridyl preferably substituted by lower alkyl or halogen. Optionally substituted thienyl represents 2- or 3-thienyl, or 2- or 3-thienyl preferably substituted by lower alkyl or halogen.

The term "biaryl" represents phenyl substituted by carbocyclic aryl or heterocyclic aryl as defined herein, ortho, meta or para to the point of attachment of the phenyl ring, advantageously para; biaryl is also represented as the —$C_6H_4$-Ar substituent where Ar is aryl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, refer to the groups —NRR' wherein respectively, (a) R is alkyl and R' is hydrogen, aryl or alkyl; (b) R is aryl and R' is hydrogen or aryl, and (c) R is aralkyl and R' is hydrogen or aralkyl.

The term "acylamino" refers to RC(O)NR'.

The term "carbonyl" refers to —C(O)—.

The term "carboxamide" or "carboxamido" refers to —CONR$_2$ wherein each R is independently hydrogen, lower alkyl or lower aryl.

The term "alkyl" refers to saturated aliphatic groups including straight-chain, branched chain and cyclic groups.

The term "alkenyl" refers to unsaturated alkyl groups which contain at least one carbon-carbon double bond and includes straight-chain, branched-chain and cyclic groups.

The term "alkynyl" refers to unsaturated alkyl groups which contain at least one carbon-carbon triple bond and includes straight-chain, branched-chain and cyclic groups.

The term "amidino" refers to —C(NH)NH$_2$.

The term "amidoximo" refers to —C(NOH)NH$_2$.

The term "mercapto" refers to SH or a tautomeric form thereof.

The term "alkylene" refers to a divalent straight chain or branched chain saturated aliphatic radical.

The term "sulfonamido" means —SO$_2$NHR where R is hydrogen or lower alkyl.

The term "N-sulfonyl amine" means —NHSO$_2$R where R is fluoro, lower perfluoroalkyl or lower alkyl.

The term "N-acylated sulfonamide" refers to the group —SO$_2$NHCOR where R is lower alkyl or lower perfluoroalkyl.

The term "basic nitrogen" generally refers to the nitrogen atom of an alkyl amine and implies a compound whose conjugated acid in aqueous solution has a pKa in the range of 9 to 11.

The term "prodrug" refers to any compound that may have less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein as examples. The groups illustrated are exemplary, not exhaustive and one skilled in the art could prepare other known varieties of prodrugs. Such prodrugs of the compounds of the invention, fall within the scope of the invention.

The term "pharmaceutically acceptable salt" includes salts of compounds described herein derived from the combination of a compound of this invention and an organic or inorganic acid. The compounds of the present invention are useful in both free base and salt form. In practice the use of salt form amounts to use of base form; both forms are within the scope of the present invention.

The term "treatment" includes prophylatic or therapeutic administration of compounds of the invention, for the cure or amelioration of disease or symptoms associated with disease, and includes any benefit obtained or derived from the administration of the described compounds.

A water solubilizing group is a group that increases the solubility of the inhibitor by a factor of at least 10 and preferably of 100 at pH values suitable for intravenous administration (pH 4 to 10).

DETAILED DESCRIPTION OF THE INVENTION

The invention relates to adenosine kinase inhibitors of the general Formula I.

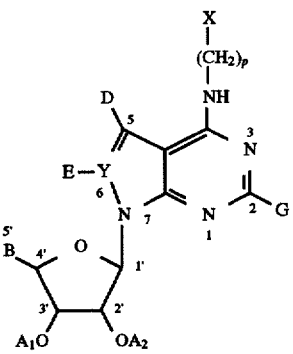

Formula 1 wherein:

A$_1$ and A$_2$ are each hydrogen or acyl, or together form a cyclic carbonate;

B is CH$_3$, alkenyl, or, (CH$_2$)$_n$—B', where n is from 1 to 4 and B' is hydrogen, hydroxy, alkyl, alkoxy, amino, azido, halogen, or alkenyl;

D is halogen, alkynyl, haloalkyl, cyano, carboxamido, or (CH$_2$)$_q$X where q is from 0 to 3 and each X is independently an aryl group, more preferably an aromatic ring optionally containing a nitrogen, sulfur, or oxygen atom optionally substituted at any position by halogen, alkyl, alkoxy, substituted per halo lower alkyl, sulfonamide, cyano, CONRR' where R and R' are independently hydrogen or lower alkyl, or is a water solubilizing group (CH$_2$)$_r$T where r is from 0 to 3 and T is an alkyl chain of 0 to 16 carbon atoms containing one or more nitrogen atoms and optionally one or more oxygen atoms, N-sulfonylated amino, amidoximo, N-aminoguanidino, amidino, guanidino, cyclic derivatives of amidines and guanidines, acylated sulfonamide, a 5 or 6 membered alicyclic ring containing nitrogen and optionally one or more oxygen atoms or CONR$_2$R$_3$ where at least one of R$_2$ and R$_3$ contains an alkyl chain containing one or more basic nitrogen atoms and optionally oxygen or taken together form a 5- or 6- membered ring containing at least one basic nitrogen.

Y is carbon or nitrogen; and E is nothing when Y is nitrogen, and is hydrogen or halogen when Y is carbon; G is hydrogen or halogen; p is from 0 to 3, preferably 0;

and pharmaceutically acceptable salts thereof;

provided at least one X includes a water solubilizing group as defined above or a nitrogen containing heterocycle.

For convenience, the numbering scheme in Formula 1 is given for pyrrolo pyrimidine compounds (Y=C). It will be understood that the nomenclature and numbering scheme is different for the pyrazolo pyrimidine (Y=N) embodiments of the invention. The compounds of the invention are potent and water soluble adenosine kinase inhibitors, and are suitably non-toxic.

Preferably, X is a substituted six member ring (phenyl) or a nitrogen-containing heterocyclic aryl. The most preferred substitution is at position 4, and the preferred water solubilizing substituents (T) are an alkyl chain of 1 to 16 carbon atoms containing one or more nitrogen atoms and optionally containing one or more oxygen atoms or a 5 or 6 membered alicyclic ring containing nitrogen or $CONR_2R_3$ where $R_2$ and $R_3$ are as defined above, or guanidino containing groups, or amidino containing groups. In theory, substitution of the ring structure as described, for example at the para position of a phenylamino group (i.e. 4-N-(4-substituted phenyl) amino) provides enhanced water solubility which in turn makes the compounds advantageous for administration to an animal. Also preferred are embodiments where $G$, $A_1$ and $A_2$ are hydrogen, B is $CH_2OH$, $CH_2NH_2$ and most preferably $CH_3$. D is preferably aryl (q=0), most preferably phenyl or phenyl substituted with $(CH_2)_rT$, where r is from 0 to 3 and T is as defined above. E is preferably hydrogen when Y=C.

In another embodiment, preferred compounds are diaryls, meaning compounds of Formula 1 where D is $(CH_2)_qX$, both X groups are independently an optionally substituted carbocyclic or heterocyclic aryl, preferably with 5 or 6 atoms in the ring. At least one X group includes water solubilizing groups or substituents, as defined above.

Prodrugs of these compounds are within the scope of this invention. Prodrugs may be prepared by esterification of the hydroxyl groups on the ribofuranose or lyxofuranose ring. Specially preferred will be the ester derivatives that further improve the water solubility properties of the resulting prodrug. The compounds of the invention also contain asymmetric carbon atoms and can exist as stereoisomers, i.e. enantiomers and diastereomers. Individual stereoisomers and mixtures thereof are within the scope of the invention. Thus, the 5'-modified 1-β-D-ribofuranosyl isomer is preferred; however the lyxofuranosyl form of these compounds (Formula 1) are within the scope of the invention.

Synthesis of Adenosine Kinase Inhibitors

The compounds of the invention can be made by several methods and for convenience can be grouped as pyrrolo or pyrazolo pyrimidines. Exemplary synthetic routes are given below.

Synthesis of Pyrrolo Pyrimidines

The pyrrolo pyrimidines of this invention have been synthesized by preparation of aryl-functionalized nucleosides, which at different stages are manipulated in order to incorporate water solubilizing groups as illustrated in the examples. As it will be clear to one skilled in the art, a number of sequences is available for the required functional group manipulations and the examples below are only an illustration of the manner in which such transformations can be carried out.

EXAMPLE 1

Preferred Synthesis of Pyrrolo Pyrimidines

Water soluble diaryl pyrrolo[2,3-d]pyrimidine nucleosides of the invention can be made according to the routes outlined in Schemes 1 and 2. The heterocycle, 5-aryl-4-arylaminopyrrolo[2,3-d]pyrimidine (Scheme 1) is made starting from a substituted phenacyl chloride or bromide by reaction with potassium phthalimide in a solvent such as N,N-dimethylformamide or acetonitrile at ambient temperature. The resulting phenacylphthalimide (3) is condensed with malononitrile in the presence of sodium methoxide to provide the 2-amino-3-cyano-4-arylpyrrole intermediate (4). Refluxing (4) with triethyl orthoformate leads to intermediate (5).

Water solubilizing groups can be incorporated at this point by reaction of (5) with an aniline which contains a desired water solubilizing group, as in Example 2B. Alternatively, the aniline may be substituted with a group that is amenable to modification, as in Example 2C. Intermediates obtained in this manner can be manipulated at later stages by well known methods. (e.g. Example 4). The desired 5-substituted-5-deoxy ribose analogs are prepared by tosylation of a suitably protected ribose, displacement of the tosylate by appropriate nucleophiles, such as hydride or azido, and subsequent deblocking (Scheme 4). Snyder, J: Serianni, A; Carbohydrate Research 163:169(1987).

SCHEME 1

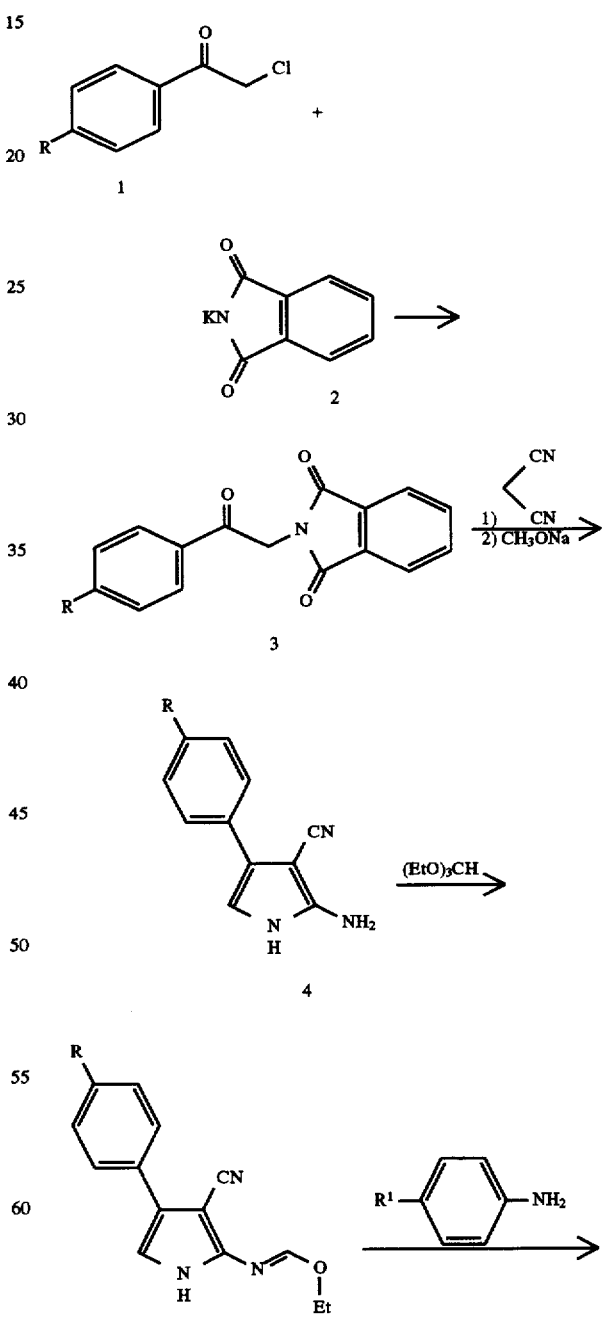

-continued
SCHEME 1

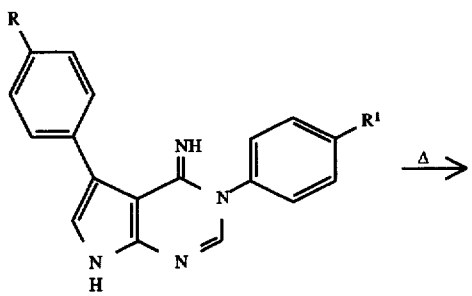

The required 1-alpha-chloro-5-deoxy-5-modified-2,3-isopropylidene-D-ribofuranose (7) is generated by reacting a sugar such as (8) with $CCl_4$ and HMPT at 0 C in toluene. Wilcox, C; Otaski, R; Tetrahedron Lett. 27:1011(1986) (Scheme 2). Reaction of (7) with the heterocycle (6) in the presence of KOH and a phase transfer catalyst such as TDA-1 at ambient temperature results in the formation of a protected nucleoside (9) Rosemeyer, H; Seela, F; Helvetica Chimica Acta, 71, 1573(1988). Deprotection under acidic conditions leads to the target compound (10).

SCHEME 2

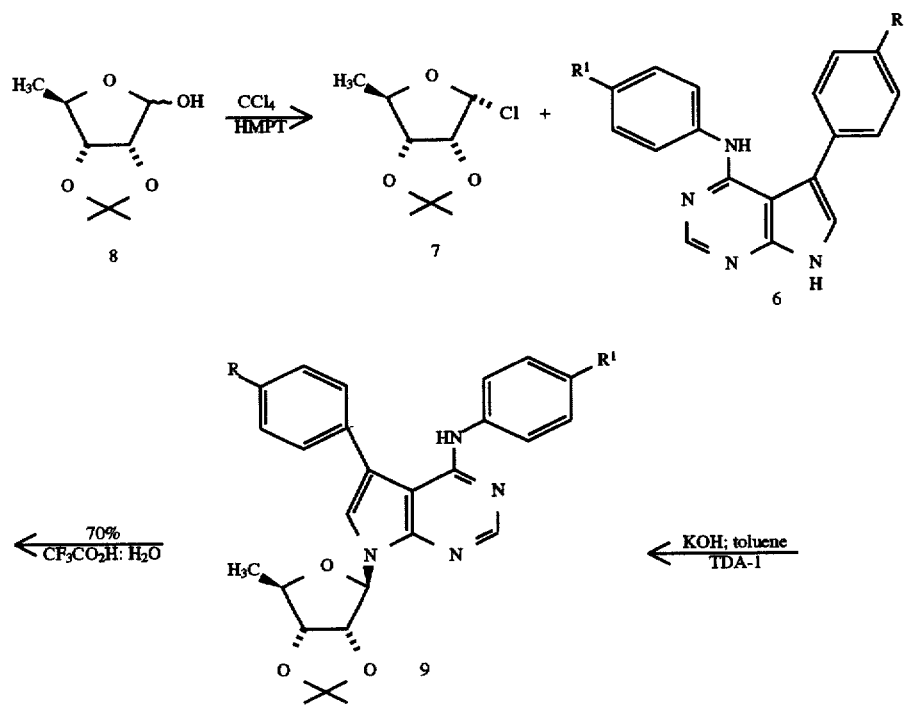

-continued
SCHEME 2

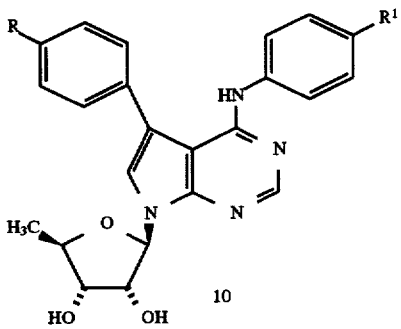

The following compounds were made by this route.
1) 4-N(N,N-Dimethylaminomethylphenyl)amino-5-phenyl-7-(5-deoxy-β-D-ribofuranosyl)pyrrolo[2,,3-d]pyrimidine.
2) 4-N(4-(2-Hydroxyethyl)phenyl)amino-5-phenyl-7-(5-deoxy-β-D- ribofuranosyl)pyrrolo[2,3-d]pyrimidine.

Other dialkylamino substituted adenosine kinase inhibitors were synthesized by reacting 4-(4-(2-hydroxyethyl)phenyl)amino-5-phenyl-7-(5-deoxy-2,3-O-isopropylidene-1-β-D-ribofuranosyl)pyrrolo[2,3-d]pyrimidine with methyl triphenoxyphosphonium iodide to provide 4-N-(2-iodoethylphenyl)amino-5-phenyl-7-(5- deoxy-β-D-ribofuranosyl)pyrrolo[2,3-d]pyrimidine. Displacement of the iodide with appropriate amines followed by acetonide group removal led to the final product compounds:

3) 4-N[2-(4-morpholino)ethylphenyl]amino-5-phenyl-7-(5-deoxy-β-D- ribofuranosyl)pyrrolo[2,3-d]pyrimidine.
4) 4-N[2-(1-piperazino)ethylphenyl]amino-5-phenyl-7-(5-deoxy-β-D- ribofuranosyl)pyrrolo[2,3-d]pyrimidine.
5) 4-N[2-(2-N,N-diethylaminoethyleneamino) ethylphenyl]amino-5-phenyl-7- (5-deoxy-β-D-ribofuranosyl)pyrrolo[2,3-d]pyrimidine.
6) 4-N[2-N,N-diethylaminoethylphenyl]amino-5-phenyl-7-(5-deoxy-β-D- ribofuranosyl)pyrrolo[2,3-d]pyrimidine.
7) 4-N[2-N,N-dimethylaminoethylphenyl]amino-5-phenyl-7-(5-deoxy-β-D- fibofuranosyl)pyrrolo[2,3-d]pyrimidine.

Synthesis of 4-N-(2-aminoethylphenyl)amino-5-phenyl-7-(5-deoxy-β-D-ribofuranosyl)pyrrolo[2,3-d]pyrimidine was achieved by subjecting the intermediate 4-N-(2-hydroxyethylphenyl)amino-5-phenyl-7-(5-deoxy-2,3-O-isopropylidine-β-D- ribofuranosyl)pyrrolo[2,3-d] pyrimidine to a Mitsunobu amination reaction using triphenyl phosphine, diisopropyl diazodicarboxylate and phthalimide. The resulting phthalimido derivative was treated with hydrazine hydrate followed by deblocking with 70% trifluoroacetic acid to yield the final product.

EXAMPLE 2

Diaryl Pyrrolopyrimidine Nucleosides

A. 2-Amino-3-cyano-4-phenylpyrrole, (4).

To a solution of phenacyl chloride (1) (500 g, 3.23 mol) in dry N,N-dimethylformamide(600 mL) was added potassium phthalimide, (2) (600 g, 3.23 mol) in small portions (Scheme 1 ). The resulting mixture was stirred at ambient temperature overnight. To this was added malononitrile (256 g, 3.88M) in one lot followed by a 25 wt % solution of sodium methoxide in methanol (744 mL, 3.2 mol). The resulting mixture was stirred at room temperature overnight. Ice-water (10.0 L) was added to the reaction mixture and stirring was continued at room temperature overnight. The precipitate formed was collected by filtration and washed with cold water (4.0 L). The off-white solid was stirred in toluene (3.0 L) and filtered. The solid was washed with toluene (300 mL) and dried under vacuum at 60 C. overnight. Yield 298.56 g. m.p. 172–174 C.

B. 4-N-(4-N,N-Dimethylaminomethylphenyl)amino-5-phenylpyrrolo[2,3-d]pyrimidine (6).

A mixture of (4) (3.66 g, 20 mmol) and triethyl orthoformate (25 mL) was refluxed for 1 h. The triethyl orthoformate was distilled off under reduced pressure until the pot temperature reached 88C. To the cooled reaction mixture hexane (100 mL) was added under vigorous stirring. The contents of the vessel were cooled to 0 C. and the off white solid formed was collected by filtration and washed with hexane (2×50 mL) and dried under suction. Final drying was done in a high vacuum oven. Yield of the 2-ethoxymethylene-3-cyano-4-phenylpyrrole (5) was 3.68 g. (m.p. 208°–209° C.)

The above material (3.67 g) was dissolved in dry N,N-dimethylformamide and 4-N,N-dimethylaminomethylaniline (5.2 g 35 mmol) was added, and the reaction mixture was heated to reflux for 1 h. Water (20 mL) was added and refluxing was continued overnight. Upon cooling to 0 C. the title compound precipitated as a brown solid which was collected by filtration and dried under vacuum. The product was crystallized from boiling ethyl acetate to provide the title compound (6). Yield 5.0 g. m.p. 208–209 C.

C. 4-N-(4-Hydroxyethylphenylamino)-5-phenyl-pyrrolo[2,3-d]pyrimidine

This compound was made by a procedure similar to the one given for (6) except that 4-N,N-dimethylaminomethylaniline was replaced with 4-hydroxyethylaniline. m.p. 178–179 C.

EXAMPLE 3

Glycosylation of Pyrrolopyrimidine Heterocycles

The procedure described here for the glycosylation of 4-N-(4-N,N-dimethylaminomethyl)phenylamino-5-phenylpyrrolo[2,3-d]pyrimidine (6) typifies a general method of glycosylation for all the pyrrolopyrimidine heterocycles.

Into a 250 mL three neck flask fitted with a thermometer, an addition funnel and a mechanical stirrer, was taken a mixture of toluene (15.0 mL), 5-deoxy-2,3-isopropylidene-D-ribofuranose (1.7 g, 10 mmol) and carbon tetrachloride (1.2 mL). The reaction mixture was cooled to −12 C. by immersing the flask into a dry ice-acetone mixture. To it was added dropwise through the addition funnel hexamethylphosphorous triamide (2.2 ml) over a period of 10 min. After the addition was completed the mixture was stirred at −10 C. for 15 min and the contents were transferred to a separatory funnel, extracted with ice cold water (1×25 mL), and the organic layer was dried over magnesium sulfate. The drying agent was removed by filtration and the filtrate was added directly to an already stirring mixture of the heterocycle (6) (1.7 g, 5 mmol), KOH (0.6 g), and TDA-1 in toluene at room temperature. Completion of the reaction was evidenced by the absence of the heterocycle on t.l.c. (SiO2, 9:1 dichloromethane-methanol). The reaction mixture was transferred to a separatory funnel and extracted with water (1×25 mL). The organic layer was evaporated and the residue was purified by flash chromatography over $SiO_2$ using 19:1 methylene chloride-methanol as eluting solvent. The fast moving spot was collected and identified to be 4-N-(N,N- dimethylaminomethylphenyl)amino-5-phenyl-7-(5-deoxy-2,3-isopropylidene-β-D-ribofuranosyl)pyrrolo(2,3-d)pyrimidine (9). This product was dissolved in 70% trifluoroacetic acid and stirred at room temperature for two hours. Volatiles were evaporated under reduced pressure and the residue was coevaporated with water (2×20 mL) and with ethanol (1×20 mL). The resulting product was dissolved in water (25 mL) and neutralized with saturated sodium bicarbonate solution. The mixture was extracted with ethyl acetate (5×25 mL). Organic layers were combined, dried and evaporated. The semi solid residue was crystallized from boiling ethyl acetate to give compound #1. Yield 400 mg. m.p. 108–109 C.

EXAMPLE 4

Alternative Synthesis of Pyrrolo Pyrimidines

Compounds of the invention can also be made according to the methods described in Browne et al., Ser. No. 08/812, 916, which is incorporated by reference.

Briefly, reaction of 4-chloro-5-iodo-7-(1-β-D-5-deoxyribofuranosyl) pyrrolo[2,3-d]pyrimidine (11) with an amine in refluxing ethanol leads to the formation of a 4-(N-substituted)amino-5-iodo-7-(5-deoxy-1 -p-D-ribofuranosyl) pyrrolo[2,3-d]pyrimidine (12). This iodo compound is treated with an aryl boronic acid in the presence of a palladium catalyst to generate the targeted 4-(N-substituted)amino-5-aryl- 7-(5-deoxy-1-β-D-ribofuranosyl) pyrrolo[2,3-d]pyrimidine, which is purified by chromatography and/or recrystallization from a suitable solvent.

For example, the synthesis of 8) 4-N-(4-N-trifluoromethanesulfonylaminophenyl) amino-5-phenyl-7-(5- deoxy-1-β-D-ribofuranosyl) pyrrolo(2,3-d)pyrimidine (16)

(Scheme 3) illustrates several aspects of the above procedure. The formation of a 4-N substituted amine is exemplified by the preparation of 4-N-(4-N- acetylaminophenyl) amino-5-iodo-7-(5-deoxy-2,3-O-isopropylidene-1-β-D-ribofuranosyl)pyrrolo(2,3-d)pyrimidine (Example 5H). The incorporation of an aryl group is illustrated in Example 51 by the preparation of 4-N-(4-N-acetylaminophenyl)amino-5- phenyl-7-(5-deoxy2,3-O-isopropylidene-1-β-D-ribofuranosyl) pyrrolo(2,3-d)pyrimidine. The latter has a functional group (N-acetyl) which can be modified in order to enhance the water solubility of the target molecule by a three step sequence: (I) deacetylation under strongly basic conditions, (ii) reaction of the resulting aniline with trifluoromethane sulfonic anhydride in dichloromethane at −78° C., in order to incorporate the water solubilizing group and, (iii) removal of the isopropylidene protecting group under acidic conditions.

Another example of a functional group modification leading to enhanced solubility properties is the preparation of 4-N-(4-guanidinophenyl)amino-5-phenyl-7-(5- deoxy-1-β-D-ribofuranosyl)pyrrolo(2,3-d)pyrimidine by reaction of 4-N-(4- aminophenyl)amino-5-phenyl-7-(5-deoxy-2,3-O-isopropylidene-1-β-D- ribofuranosyl)pyrrolo(2,3-d) pyrimidine (Scheme 3, 14) with aminoiminomethane sulfonic acid followed by deprotection of the diol under acidic conditions.

SCHEME 3

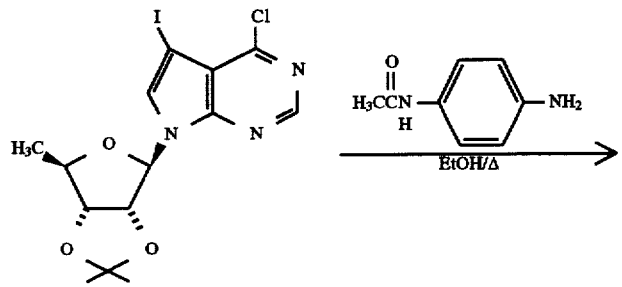

11

-continued
SCHEME 3
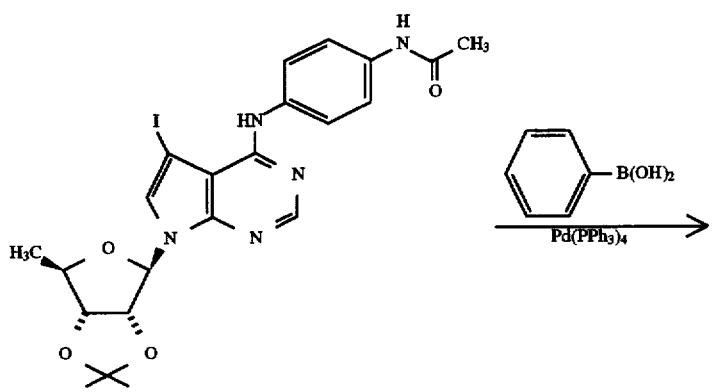
12
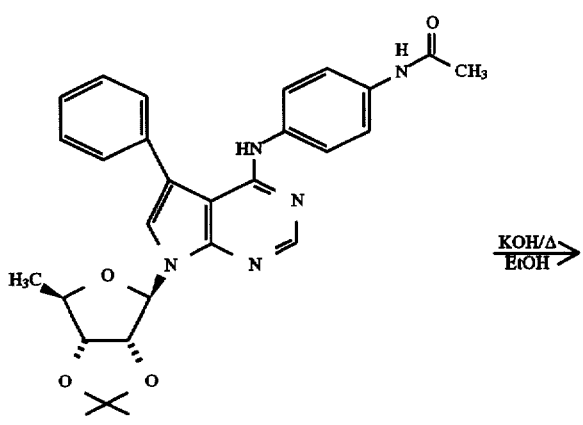
13
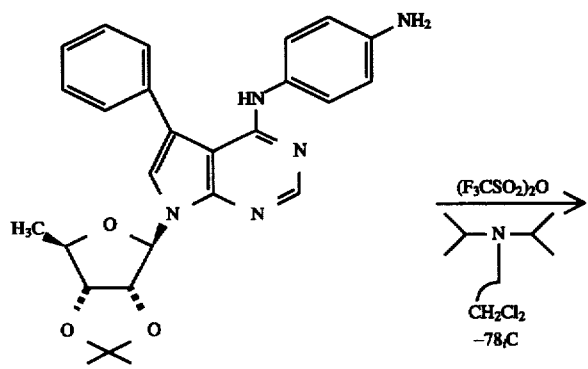
14

SCHEME 3 -continued

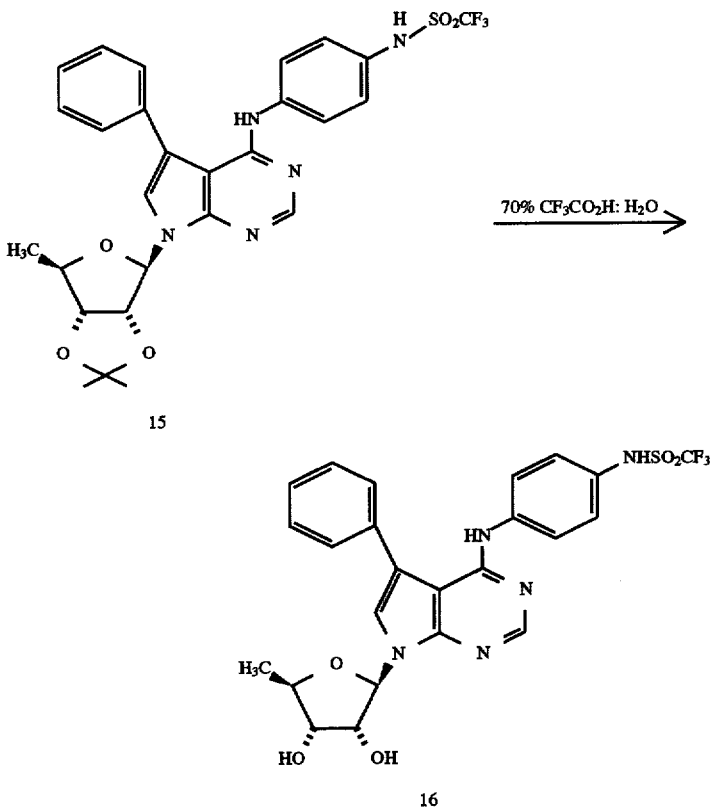

In another instance, a nitrile group can be converted to an amidine or an amidoxime group by procedures which are well established in the literature (Gabrielson et al., J. Med. Chem. 35, 3231 (1992)), as indicated by the conversion of 4-N-(4- cyanophenyl)amino-5-phenyl-7-(5-deoxy-2,3-O-isopropylidene-1-β-D-ribofuranosyl) pyrrolo(2,3-d) pyrimidine into 4-N-(4-amidinophenyl)amino-5-phenyl-7-(5-deoxy-1-β-D- ribofuranosyl)pyrrolo(2,3-d)pyrimidine or 4-N-(4-amidoximephenyl)amino-5-phenyl-7-(5- deoxy-1-β-D-ribofuranosyl)pyrrolo(2,3-d)pyrimidine or4-N-(4-amidoximephenylamino-5- phenyl-7-(5-deoxy-1-β-D-ribofuranosyl)pyrrolo(2,3-d)pyrimidine (Example 5.0).

Similarly the following L-lyxofuranosyl analogs can be synthesized by the above procedures where the ribofuranose intermediate is replaced with an appropriately protected L-lyxofuranose.

9) 4-N-(N,N-Dimethylaminomethylphenyl)amino-5-phenyl-7-α-L- lyxofuranosylpyrrolo[2,,3-d] pyrimidine.

10) 4-N-(2-Hydroxyethylphenyl)amino-5-phenyl-7-α-L-lyxofuranosylpyrrolo[2,3-d]pyrimidine.

11) 4-N-[2-(4-morpholino)ethylphenyl]amino-5-phenyl-7-α-L- lyxofuranosylpyrrolo[2,3-d]pyrimidine.

12) 4-N-[2-(1-piperazino)ethylphenyl]amino-5-phenyl-7-α-L- lyxofuranosylpyrrolo[2,3-d]pyrimidine.

13) 4-N-[2-(2-N,N-diethylaminoethyleneamino) ethylphenyl]amino-5-phenyl-7- α-L-lyxofuranosylpyrrolo[2,3-d]pyrimidine.

14) 4-N-[2-N,N-diethylaminoethylphenyl]amino-5-phenyl-7-α-L- lyxofuranosylpyrrolo[2,3-d]pyrimidine.

15) 4-N-[2-N,N-dimethylaminoethylphenyl]amino-5-phenyl-7-α-L- lyxofuranosylpyrrolo[2,3-d]pyrimidine.

16) 4-N-(2-aminoethylphenyl)amino-5-phenyl-7-α-L-lyxofuranosylpyrrolo[2,3- d]pyrimidine.

17) 4-N-(4-N-trifluoromethanesulfonylaminophenyl) amino-5-phenyl-7-α-L- lyxofuranosylpyrrolo[2,3-d] pyrimidine.

EXAMPLE 5

Preparation of Representative Compounds

Preparation of the following representative compounds is described:

18) 4-N-[2-tert-butyldimethylsilyloxyethylphenyl]amino-5-phenyl- pyrrolo[2,3-d]pyrimidine 19) 4-N-(2-tert-butyldimethylsilyloxyethylphenyl)amino-5-phenyl-7- (5-deoxy- 2,3-O-isopropylidene-β-D-ribofuranosyl)pyrrolo[2,3-d]pyrimidine 20) 4-N-(2-Hydroxyethylphenyl)amino-5-phenyl-7-(5-deoxy-β-D- ribofuranosyl)pyrrolo[2,3-d]pyrimidine 21) 4-N-(2-Hydroxyethylphenyl)amino-5-phenyl-7-(5-deoxy-2,3-isopropylidine- β-D-ribofuranosyl)pyrrolo [2,3-d]pyrimidine 22) 4-N-(2-Aminoethylphenyl)amino-5-phenyl-7-(5-deoxy-β-D- ribofuranosyl)pyrrolo[2,3-d]pyrimidine 23) 4-N-(2-Iodoethylphenyl)amino-5-phenyl-7-(5-deoxy-2,3-isopropylidene-β- D-ribofuranosyl)pyrrolo[2,3-d] pyrimidine 24) 4-N-[2-(1-Morpholino)ethlylphenyl]amino-5-phenyl-7-(5-deoxy-β-D- ribofuranosyl)pyrrolo[2,3-d] pyrimidine.

25) 4-N-[2-(4-Piperazino)ethylphenyl]amino-5-phenyl-7-(5-deoxy-β-D- ribofuranosyl)pyrrolo[2,3-d] pyrimidine. m.p. 168°–170° C.

26) 4-N-[2-(2-N,N-Diethylamino)ethylphenyl]amino-5-phenyl-7-(5-deoxy-β-D- ribofuranosyl)pyrrolo[2,3-d]pyrimidine. m.p. 97°–99° C.

27) 4-N-[2-(N,N-Diethylaminoethyleneamino) ethlylphenyl]amino-5-phenyl-7- (5- deoxy-β-D-ribofuranosyl)pyrrolo[2,3-d]pyrimidine hydrochloride m.p. 110–12 C.

28) 4-N-[2-(N,N-Dimethylamino)ethylphenyl]amino-5-phenyl-7-(5-deoxy-β-D- ribofuranosyl)pyrrolo[2,3-d]pyrimidine. m.p. 145–146 C.

29) 4-N-(4-N-Acetylaminophenyl)amino-5-iodo-7-(1-β-D-5-deoxy-2,3-O- isopropylideneribose)pyrrolo[2,3-d]pyrimidine 30) Preparation of 4-N-(4-N-Acetylaminophenyl)amino-5-phenyl-7-(1-β-D-5- deoxy-2,3-O-isopropylideneribose) pyrrolo[2,3-d]pyrimidine 31) 4-N-(3-Hydroxymethylphenyl)amino-5-phenyl-7-(5-deoxy-1-β-D- ribofuranosyl)-pyrrolo(2,3-d)pyrimidine 32) Preparation of 4-N-(4-Aminophenyl)amino-5-phenyl-7-(5-deoxy-1-β-D-2,3- O-isopropylideneribose) pyrrolo[2,3-d]pyrimidine 33) Preparation of 4-N-(4-N-trifluoromethanesulfonylaminophenyl)amino-5-phenyl-7-(5-deoxy-1-β-D-ribose)pyrrolo[2,3-d]pyrimidine 34) 4-N-(4-cyanophenyl)amino-5-iodo-7(2,3-O-isopropylidene-5-deoxy-1 -β-D- ribofuranosyl)pyrrolo[2,3-d]pyrimidine 35) 4-N-(4-cyanophenyl)amino-5-phenyl-7-(2,3-O-isopropylidene-5-deoxy-1-β- D-ribofuranosyl)pyrrolo[2,3-d]pyrimidine 36) 4-N-(4-amidoximephenyl)amino-5-phenyl-7-(2,3-O-isopropylidene-5- deoxy-1-β-D-ribofuranosyl) pyrrolo[2,3-d]pyrimidine 37) 4-N-(4-amidoximephenyl)amino-5-phenyl-7-(5-deoxy-1-β-D- ribofuranosylpyrrolo[2,3-d]pyrimidine hydrochloride 38) 4-N-(4-amidinophenyl)amino-5-phenyl-7-(2,3-O-isopropylidene-5-deoxy-1- β-D-ribofuranosyl)pyrrolo[2,3-d]pyrimidine 39) 4-N-(4-amidinophenyl)amino-5-phenyl-7-(5-deoxy-1-β-D- ribofuranosyl)pyrrolo[2,3-d]pyrimidine 40) 4-N-(4-N-acetylaminosulfonyl)phenyl)amino-5-phenyl-7-(5-deoxy-1-β-D- ribofuranosyl)pyrrolo[2,3-d]pyrimidine 41) 4-N-(2-Pyridylmethylamino)-5-iodo-7-(5-deoxy-1-β-D- ribofuranosyl)pyrrolo[2,3-d]pyrimidine Preparation of 4-N-[2-tert-butyldimethylsilyloxyethylphenyl]amino-5- phenyl-pyrrolo[2,3-d]pyrimidine (18)

To a suspension of 4-N-(2-Hydroxyethylphenyl)amino-5-phenyl- pyrrolo[2,3-d]pyrimidine (3.1 g, 9.4 mmol) and imidazole (1.27 g, 2 mmol) in dichloromethane (200 mL) was added a solution of tert-butyldimethylsilyl chloride (1.55 g, 10.3 mmol) in small portions over a 10 min period. The reaction mixture was stirred until there was no starting material seen on t.l.c. ($SiO_2$, 4:1 ethyl acetate-hexane). The reaction mixture was filtered and the solid was washed with methylene chloride (2×10 mL). The combined filtrate and washings were evaporated and chromatographed over $SiO_2$ using 4:1 ethyl acetate-hexane. Yield 3.3 g. m.p. 162–165 C. Rf=0.5 in the above solvent.

B. Preparation of 4-N-(2-tert-butyldimethylsilyloxyethylphenyl)amino-5- phenyl-7-(5-deoxy-2,3-O-isopropylidene-β-D-ribofuranosyl)pyrrolo[2,3- d]pyrimidine (19)

The above heterocycle was glycosylated with 5-deoxy-2, 3-O-isopropylidene-D-ribose (7) by the procedure described earlier for the synthesis of (1), as in Example 1. The product was obtained as a glassy solid. H-NMR, DMSO-$d_6$:, 6.3(d, 1H, $C_1$-H anomeric), 7.1–7.8(M,10H, aromatics), 8.41 (S, 1H, C-2H) 2.7 and 3.75 (2t, 4H, $CH_2$—$CH_2$-O-side chain), and other sugar protons. Rf=0.75, silica, 4:1 Ethyl acetate :hexane.

C. Preparation of 4-N-(2-Hydroxyethylphenyl)amino-5-phenyl-7-(5-deoxy-β- D-ribofuranosyl)pyrrolo[2,3-d]pyrimidine (20)

This compound was prepared by treating the above compound with 70% trifluoroacetic acid in water at room temperature and working up the reaction by the procedure described for the synthesis of (1). m.p. 221–223 C. Rf=0.45 $SiO_2$, 9:1 $CH_2Cl_2$- methanol.

D. Preparation of 4-N-(2-Hydroxyethylphenyl)amino-5-phenyl-7-(5-deoxy-2,3- isopropylidine-β-D-ribofuranosyl) pyrrolo[2,3-d]pyrimidine (21).

To a solution of 4-N-(2-tert-butyldimethylsilyloxyethylphenyl)amino-5- phenyl-7-(5-deoxy-β-D-ribofuranosyl)pyrrolo[2,3-d]pyrimidine (2.1 g) in dry THF (75 mL) was added 1M solution of tetrabutylammonium fluoride (5.0 mL) at 0 C. The reaction mixture was stirred at room temperature overnight. Solvent evaporated and residue was purified by chromatography over $SiO_2$ using 4:1 ethyl acetate-hexane. The product was obtained as a glassy solid. Rf=0.7 in the above solvent system.

E. Preparation of 4-N-(2-Aminoethylphenyl)amino-5-phenyl-7-(5-deoxy-β-D- ribofuranosyl)pyrrolo[2,3-d]pyrimidine (22)

To a stirred solution of a compound of 4-N-(2-Hydroxyethylphenyl)amino- 5-phenyl-7-(5-deoxy-2,3-isopropylidene-β-D-ribofuranosyl)pyrrolo[2,3-d] pyrimidine (Example 5C), (242 mg), phthalimide (110 mg) and triphenylphosphine (196 mg) in dry tetrahydrofuran (7.0 mL) diisopropyldiazodicarboxylate (0.16 mL) was added and stirred for 16 hours. Completion of the reaction was evidenced by the absence of the starting material on the t.l.c. Volatiles were evaporated and the residue was purified by chromatography on a $SiO_2$ gel column. The product thus obtained was dissolved in ethanol (10 mL) containing hydrazine (0.2 mL of 97%) and refluxed for 3 hours. The reaction mixture was cooled and filtered and the filtrate was evaporated to obtain a semi solid which was deblocked with methanol (5 mL) and 1N aq. HCl (5 mL) under refluxing conditions for 20 min. The reaction mixture was cooled and treated with 2N NaOH solution to adjust the pH to 8. The reaction mixture was extracted repeatedly with ethyl acetate (4×25 mL). The combined organic layers was dried over magnesium sulfate and evaporated to obtain an off white solid which was crystallized from boiling ethanol. Yield 115 mg, m.p. 192–193 C.

F. Preparation of 4-N-(2-Iodoethylphenyl)amino-5-phenyl-7-(5-deoxy-2,3- isopropylidene-β-D-ribofuranosyl)pyrrolo[2,3-d]pyrimidine (23)

To a solution of 4-(2-Hydroxyethylphenyl)amino-5-phenyl-7-(5-deoxy-2,3- isopropylidene-β-D-ribofuranosyl) pyrrolo[2,3-d]pyrimidine (1.0 g, 2.1 mmol) in methylene chloride (37 mL) methyl triphenoxyphosphonium iodide (2.05g, 4.7 mmol) was added and stirred at room temperature. After two hours completion of the reaction was evidenced by t.l.c. ($SiO_2$, 2:1 hexane-ethyl acetate). The reaction was quenched with methanol (200 μL), extracted with 0.5M solution of sodium thiosulfate (20 mL) and with water (20 mL). The organic layer was dried over sodium sulfate and evaporated to obtain an oily residue which was purified by chromatography over $SiO_2$ using 4:1 hexane-ethyl acetate as eluting solvent to obtain the title compound as a glassy solid. Yield 1.4 g. T.l.c. $SiO_2$, 2:1 hexane-ethyl acetate, Rf=0.25.

G. Preparation of 4-N-[2-(1-Morpholino)ethlylphenyl]amino-5-phenyl-7-(5- deoxy-β-D-ribofuranosyl)pyrrolo[2,3-d]pyrimidine (24)

A mixture of the above iodo compound of Example 3E (76 mg, 0.18 mmol), morpholine (0.1 mL) and dioxane (5 mL) was refluxed overnight. Volatiles were removed under high vacuum and the residue was chromatographed over silica gel using 19:1 hexane-ethyl acetate. The intermediate thus obtained was subjected to deblocking by gently refluxing it with methanol (2.0 mL) and 0.5N HCl solution (5.0 mL) for 30 min. The reaction mixture was cooled and the pH was adjusted to ~8 by adding 1M $KHCO_3$ solution. The precipitate was collected by filtration, washed with water, and dried in air. The product was crystallized from boiling ethyl acetate. Yield 30 mg. m.p. 95–100 C.

The following compounds were also synthesized as described above:

25) 4-N-[2-(4-Piperazino)ethylphenyl]amino-5-phenyl-7-(5-deoxy-β-D- ribofuranosyl)pyrrolo[2,3-d]pyrimidine. m.p. 168°–170° C.

26) 4-N-[2-(2-N,N-Diethylamino)ethylphenyl]amino-5-phenyl-7-(5-deoxy-β-D- ribofuranosyl)pyrrolo[2,3-d]pyrimidine. m.p. 97°–99° C.

27) 4-N-[2-(N,N-Diethylaminoethyleneamino)ethlylphenyl]amino-5-phenyl-7- (5- deoxy-β-D-ribofuranosyl)pyrrolo[2,3-d]pyrimidine hydrochloride m.p. 110–12 C.

28) 4-N-[2-(N,N-Dimethylamino)ethylphenyl]amino-5-phenyl-7-(5-deoxy-β-D- ribofuranosyl)pyrrolo[2,3-d]pyrimidine. m.p. 145–146 C.

H. Preparation of 4-N-(4-N-Acetylaminophenyl)amino-5-iodo-7-(1-β-D-5- deoxy-2,3-O-isopropylideneribose)pyrrolo[2,3-d]pyrimidine (29)

A mixture of 848 mg (1.87 mmol) of 4-chloro-5-iodo-7-(5-deoxy-2,3-O- isopropylidene-1-β-D-ribofuranosyl)pyrrolo[2,3-d]pyrimidine and 580 mg (3.86 mmol) of 4-aminoacetanilide in 50 mL of ethanol was heated to reflux for 15 h. The solvent was evaporated under reduced pressure and the residue dissolved in ethyl acetate and washed with water and saturated aqueous sodium chloride solution. Dried over magnesium sulfate and evaporated under reduced pressure. Chromatography on silica gel using 4% methanol in dichloromethane afforded 610 mg (57%) of the title compound. HNMR (200 MHZ, DMSO-$d_6$): 9.93 (s, 1H), 8.33 (s,1H) 8.17 (s, 1H), 7.81 (s, 1H), 7.60 (AB quartet, 4H), 6.17 (d, J=3.1 Hz, 1H), 2.03 (s, 3H), 1.51 (s, 3H), 1.30 (s, 3H), 1.26 (d, J=6.5 Hz, 3H).

I. Preparation of 4-N-(4-N-Acetylaminophenyl)amino-5-phenyl-7-(1-β-D-5- deoxy-2,3-O-isopropylideneribose) pyrrolo[2,3-d]pyrimidine (30)

A solution of 560 mg (0.99 mmol) of 4-(4-N-acetylaminophenyl)amino-5- iodo-7-(1-β-D-5-deoxy-2,3-O-isopropylideneribose)pyrrolo[2,3-d]pyrimidine, 626 mg (5.13 mmol) of phenylboric acid and 240 mg (0.21 mmol) of palladium tetrakistriphenylphosphine in 9 mL of diglyme was treated with 6 mL of saturated aqueous sodium carbonate solution and heated at 100 C. for 5h. The mixture was cooled to room temperature, filtered through a celite pad and partitioned between ethyl acetate and water. The organic layer was washed with water and saturated sodium chloride solution, dried over magnesium sulfate and evaporated under reduced pressure at 50 C. Chromatography on silica gel eluting with 3% methanol in dichloromethane afforded 507 mg of the title product. HNMR (200 MHZ, DMSO-$d_6$): 9.87 (s, 1H), 8.38 (s, 1H), 6.28 (d,, J=3.0 Hz), 2.00 (s, 3H), 1.54 (s, 3H), 1.31 (s, 3H), 1.29 (d, J=7.2 Hz).

The following compound was made by the above two step procedure, by substituting 3-hydroxymethylaniline for 4-aminoacetanilide in the first step.

31) 4-N-(3-Hydroxymethylphenyl)amino-5-phenyl-7-(5-deoxy-1-β-D- ribofuranosyl)-pyrrolo(2,3-d) pyrimidine. m.p. 192–193 C.

J. Preparation of 4-N-(4-Aminophenyl)amino-5-phenyl-7-(5-deoxy-2,3-O- isopropylidene-1-β-D-ribofuranosyl) pyrrolo[2,3-d]pyrimidine (32)

A solution of 440 mg (0.85 mmol) of 4-(4-acetylaminophenyl)amino-5- phenyl-7-(-5-deoxy-2,3-O-isopropylidenene-1 -β-D-ribofuranosyl)pyrrolo[2,3-d]pyrimidine and 912 mg of KOH in 50 mL of ethanol was heated to reflux for a period of 140 h. The mixture was cooled to room temperature and partitioned between water and methylene chloride. The organic layer was washed with water and saturated sodium chloride solution, dried over $MgSO_4$ and evaporated under reduced pressure. Obtained 301 mg (72% crude yield) of a white foam which was used without further purification in the following step. HNMR (200 MHZ, DMSO-$d_6$): 8.28 (s, 1H), 7.13 (d, J=8.7 Hz, 2H) 6.50 (d, J=8.7 Hz, 2H) 6.25 (d, J=3.0 Hz, 1H), 1.53 (s, 3H) 1.31 (s, 3H), 1.29 (d, J=7.5 Hz), 3H).

K. Preparation of 4-N-(4-N-trifluoromethanesulfonylaminophenyl)amino-5- phenyl-7-(5-deoxy-1-β-D-ribofuranosyl)pyrrolo[2,3-d]pyrimidine (33).

To a mixture of 190 mg (0.39 mmol) of 4-N-(4-aminophenyl)amino-5- phenyl-7-(5-deoxy-2,3-O-isopropylidenene-1 -β-D-ribofuranosyl)pyrrolo[2,3-d] pyrimidine in 20 mL of dichloromethane cooled to –78 C. was added N,N-diisopropylethylamine (140 µL, 0.80 mmol) followed by trifluoromethanesulfonic anhydride (80 µL, 0.48 mmol). The resulting reaction mixture was allowed to stir for a period of 3.5 h, when the temperature of the external bath had reached 0 C. Water was added and the organic layer was separated and washed (water and saturated sodium chloride solution), dried ($MgSO_4$) and evaporated under reduced pressure. Chromatography on silica gel using 5% methanol in methylene chloride afforded an oil which was treated with 7:3 (v:v) trifluoroacetic acid:water at room temperature for 2.5 h. The volatiles were evaporated under reduced pressure and the residue coevaporated twice with toluene. The resulting oil was treated with water and methanol. The precipitate obtained was removed by filtration, suspended in hexanes and filtered one more time. After drying for 12 h at 45 C. the resulting off-white solid had a melting point of 153–155 C.

L. Preparation of 4-N-(4-cyanophenyl)amino-5-iodo-7(5-deoxy-2,3-O- isopropylidene-1-β-D-ribofuranosyl)pyrrolo [2,3-d]pyrimidine (34)

A solution of 400 mg (0.92 mmol) of 4-chloro-5-iodo-7-(1-β-D-2,3-O- isopropylidene 5-deoxyribofuranosyl) pyrrolo[2,3-d]pyrimidine and 4-aminobenzonitrile (1.085 g, 9.18 mmol) in DMF (10 mL) at room temperature under a nitrogen atmosphere was treated with 5.0 mL (5.0 mmol) of a 1M solution of potassium t-butoxide in t-butanol. The resulting dark mixture was stirred at the same temperature for 1 h. The volatiles were removed under reduced pressure and the residue taken to pH 7 using 1N aqueous HCl solution and extracted with ethyl acetate. The organic phase was washed (water, sat NaCl solution), dried (MgSO4) and evaporated under reduced pressure. Chromatography on silica gel using 25% ethyl acetate in hexanes afforded 408 mg of the title compound. HNMR (200 MHZ, DMSO-$d_6$); 8.76(s, 1H), 8.48(s, 1H), 7.87(AB quartet, 4H), 6.20(d, J=2.6 Hz, 1H), 1.52(s, 3H), 1.30(s, 3H), 1.26(d, J=6.6Hz, 3H).

M. Preparation of 4-N-(4-cyanophenyl)amino-5-phenyl-7-(5-deoxy-2,3-O- isopropylidene-1-β-D-ribofuranosyl) pyrrolo[2,3-d]pyrimidine (35)

A mixture of 4-N-(4-cyanophenyl)amino-5-iodo-7-(5-deoxy-2,3-O- isopropylidene-1-62-D-ribofuranosylpyrrolo [2,3-d]pyrimidine (408 mg, 0.79 mmol), phenyl boric acid (433 mg, 3.55 mmol), palladium tetrakistriphenylphosphine (110 mg, 0.09 mmol) and 5 mL of a saturated solution of sodium carbonate in 25 mL of diglyme was heated to 90° C. for 2 h. After cooling to room temperature and filtering through a celite pad, the solvent was evaporated and the residue chromatographed on silica using 20% ethyl acetate in hexanes as the eluent. Obtained 334 mg of the title compound with Rf=0.30 (20%ethyl acetate in hexanes, silica).

N. Preparation of 4-N-(4-amidoximephenyl)amino-5-phenyl-7-(5-deoxy-2,3- O-isopropylidene-1-β-D-ribofuranosyl) pyrrolo[2,3-d]pyrimidine (36)

A solution of 4-N-(4-cyanophenyl)amino-5-phenyl-7-(5-deoxy-2,3-O- isopropylidene-5-deoxyribofuranosyl) pyrrolo[2,3-d]pyrimidine (162 mg, 0.35 mmol) in THF (15 mL) was treated with a solution of 250 mg (0.35 mmol) of hydroxylamine hydrochloride and 14 mg (0.35 mmol) of sodium hydroxide in 5 mL of water. The mixture was heated to reflux for 96 h. The THF was removed under reduced pressure and the residue partitioned between ethyl acetate and water. The organic layer was washed (water, saturated sodium chloride solution), dried (MgSO4) and evaporated. Chromatography on silica gel using 5% methanol in dichloromethane afforded 141 mg of product.

O. Preparation of 4-N-(4-amidoximephenyl)amino-5-phenyl-7-(1-β-D-5- deoxyribofuranosyl)pyrrolo[2,3-d] pyrimidine hydrochloride (37)

A solution of 4-N-(4-amidoximephenyl)amino-5-phenyl-7-(5-deoxy-2,3-O- isopropylidene-1-β-D-ribofuranosyl) pyrrolo[2,3-d]pyrimidine (141 mg) in 10 mL of methanol saturated with hydrogen chloride was stirred at room temperature for a period of 1 h. Removal of the volatiles left a foam which was crystallized from methanol-ether. The resulting off white solid had m.p. 173°–178° C.

P. Preparation of 4-N-(4-amidinophenyl)amino-5-phenyl-7-(5-deoxy-1-β-D- ribofuranosyl)pyrrolo[2,3-d]pyrimidine (38)

The title compound is prepared by treating 4-N-(4-amidoximophenyl)amino-5-phenyl-7-(5-deoxy-1 -β-D-ribofuranosyl)pyrrolo[2,3- d]pyrimidine as described by Srivasta et al. *J. Med. Chem.* 19:1020 (1976).

R. Preparation of 4-N-(4-N-acetylaminosulfonyl)phenyl) amino-5-phenyl-7-(5- deoxy-1-β-D-ribofuranosyl)pyrrolo [2,3-d]pyrimidine (40).

To a solution of 4-N-(4-sulfonamidophenyl)amino-5-phenyl-7-(5-deoxy-2,3- O-isopropylidene-1-β-D-ribofuranosyl)pyrrolo[2,3-d]pyrimidine (293 mg, prepared by the methods illustrated in examples 5H–5I) in 15 mL of tetrahydrofuran at room temperature was added 0.61 mL of a 1.0M solution of potassium t-butoxyde in t-butanol. After stirring for 1.5 h at the same temperature, acetic anhydride (0.10 mL) was added and the solution stirred for an additional 10 min. The reaction was treated with 10 mL of 70% trifluoroacetic acid in water and stirred at room temperature for 1 h. Evaporation of the volatiles and chromatography on silica gel (eluting with 5% methanol in dichloromethane) yielded 85 mg of title compound, m.p. 229°–231° C.

S. Preparation of 4-N-(2-Pyridylmethylamino)-5-iodo-7-(5-deoxy-1-β-D- ribofuranosyl)pyrrolo[2,3-d]pyrimidine (41)

A mixture of 2.2 mmol of 4-chloro-5-iodo-7-(5-deoxy-2, 3-O-isopropylidene- 1-β-D-ribofuranosyl) and 4.0 equivalents of 2-aminomethyl pyridine in 25 mL of ethanol were heated to reflux for a period of 24 hours. The solvent was removed under reduced pressure and the residue partitioned between ethyl acetate and water. The organic layer was washed with water and then with a saturated solution of sodium chloride. Dried over sodium sulfate and evaporated under reduced pressure to obtain 515 mg (83%) of a waxy yellow solid whose HNMR had a diagnostic doublet at 6.14 ppm (J=2.9Hz). This product was treated with 20 mL of a 7:3 mixture of trifluoroacetic acid and water at room temperature for 90 min. The reaction mixture was evaporated under reduced pressure, dissolved in methanol and stirred for 15 minutes in the presence of an excess of potassium carbonate. The potassium carbonate was filtered, the solvent removed and the residue chromatographed on silica using 5% methanol in methylene chloride to afford a white solid with Rf=0.28 (5% $CH_3OH$ in $CH_2Cl_2$; silica). Crystallized from methanol-ether to obtain 445 mg (43%) of the title compound with melting point 199–202 C.

Other compounds prepared by similar procedures:

42) 4-N-(4-pyridylmethylamino)-5-iodo-7-(5-deoxy-1-β-D- ribofuranosyl)pyrrolo[2,3-d]pyrimidine. Off-white solid. Melting point: 110–111 C. Rf=0.60 (10% $CH_3OH$ in $CH_2Cl_2$).

43) 4-N-(2-(2-pyridylethyl)amino)-5-iodo-7-(5-deoxy-1-β-D- ribofuranosyl)pyrrolo[2,3-d]pyrimidine. Melting point: 179–181 C.

44) 4-N-(3-pyridylmethylamino)-5-iodo-7-(5-deoxy-1-β-D- ribofuranosyl)pyrrolo[2,3-d]pyrimidine. White solid. Melting point: 135–138 C. Rf=0.28 (5% $CH_3OH$ in $CH_2Cl_2$)

45) 4-N-(2-benzimidazolylmethyl)amino-5-iodo-7-(5-deoxy-1-β-D- ribofuranosyl) pyrrolo[(2,3-d)]pyrimidine. White solid. Melting point: 203–205 C. Rf=0.49 (10% $CH_3OH$ in $CH_2Cl_2$).

46) 4-N-(2-pyridylmethyl)amino-5-iodo-7-(α-L-lyxofuranosyl)pyrrolo(2,3- d)pyrimidine. m.p. 214–216 C.

The intermediates 5-iodo-4-(N-phenyl)amino-7-(5-deoxy-2,3-isopropylidene-β-D- ribofuranosyl)pyrrolo[2,3-d]pyrimidine and 5-iodo-4-(3-pyridyl)amino-7-(5-deoxy-2, 3-isopropylidene-β-D-ribofuranosyl)pyrrolo[2,3-d] pyrimidine can also be prepared in a similar manner.

EXAMPLE 6

Additional Pyrrolo Pyrimidines of the Invention

Preparation of the following additional compounds of the invention is described in this example.

47) 4-N-Phenylamino-5-(3-pyridino)-7-(5-deoxy-1-β-D-ribofuranosyl) pyrrolo[2,3-d]pyrimidine 48) 4-N-(2-pyridylmethyl)amino-5-(3-pyridino)-7-(5-deoxy-1-β-D- ribofuranosyl)pyrrolo[2,3-d]pyrimidine. solid. m.p. 189–192 C.

49) 4-N-(4-pyridylmethyl)amino-5-phenyl-7-(5-deoxy-1-β-D-ribofuranosyl)- pyrrolo[2,3-d]pyrimidine. m.p. 103–108 C.

50) 4-N-(3-pyridylmethyl)amino-5-phenyl-7-(5-deoxy-1-β-D-ribofuranosyl)- pyrrolo[2,3-d]pyrimidine. m.p. 211–212 C.

51) Preparation of 4-N-((methylphosphoryloxy)phenyl) amino-5-phenyl-7-(5- deoxy-1-β-D-ribofuranosyl) pyrrolo[2,3-d]pyrimidine A. Preparation of 4-N-Phenylamino-5-(3-pyridino)-7-(5-deoxy-1-β-D- ribofuranosyl) pyrrolo[2,3-d]pyrimidine (47)

A mixture of 0.35 mmol of 5-iodo-4-N-phenylamino-7-(5-deoxy-2,3-O- isopropylidene1-β-D-ribofuranosyl) pyrrolo[2,3-d]pyrimidine, 4.4 equivalents of 3-pyridyiboronic acid (Terashima et al., *Chem. Pharm. Bull.* 31, 4573 (1983)) and 0.16 equivalents of tetrakis triphenylphosphine palladium in a 10 mL of diglyme and 4 mL of ethanol was treated with 2 mL of a saturated sodium carbonate solution and heated to 100° C. for approximately 5 hours. The mixture was allowed to cool to room temperature, an excess of ethyl acetate was added, and the organic layer was washed with diluted sodium bicarbonate solution, water and saturated sodium chloride. The resulting solution was dried over sodium sulfate and evaporated under reduced pressure. The residue was chromatographed on silica using a 3% solution of methanol in methylene chloride to obtain 131 mg of a brown oil with Rf=0.38 (3% $CH_3OH$ in $CH_2Cl_2$). This oil was stirred at room temperature for 30 min in 70% trifluoroacetic acid:water mixture. The solvent was evaporated under reduced pressure and the residue stirred in methanolic $K_2CO_3$ for 5 minutes, filtered through a celite pad and coevaporated with toluene. Filtration through a silica pad using 10% $CH_3OH$ in $CH_2Cl_2$ as the eluent afforded after evaporation a cream colored solid that was recrystallized from methanol ether. The resulting title compound was an off-white solid with melting point 189–192 C. and Rf=0.27 (5% $CH_3OH$ in $CH_2Cl_2$).

The following compounds were also prepared in this fashion.

48) 4-N-(2-pyridylmethyl)amino-5-(3-pyridino)-7-(5-deoxy-1-β-D- ribofuranosyl)pyrrolo[2,3-d]pyrimidine. solid. m.p. 189–192 C.

49) 4-N-(4-pyridylmethyl)amino-5-phenyl-7-(5-deoxy-1-β-D-ribofuranosyl)- pyrrolo[2,3-d]pyrimidine. m.p. 103–108 C.

50) 4-N-(3-pyridylmethyl)amino-5-phenyl-7-(5-deoxy-1-β-D-ribofuranosyl)- pyrrolo[2,3-d]pyrimidine. m.p. 211–212 C.

B. Preparation of 4-N-((methylphosphoryloxy)phenyl) amino-5-phenyl-7-(1-β- D-5-deoxyribofuranosyl) pyrrolo [2,3-d]pyrimidine (51)

The compound 4-N-(4-hydroxyphenyl)amino-5-phenyl-7-(5-deoxy-2,3-O- isopyrolidene-1-β-D-ribofuranosyl) pyrrolo[2,3-d]pyrimidine was made by a procedure analogous to Example 5G, by substituting 4-aminophenol for 4-aminoacetanilide. Dimethyl phosphoryl chloridate (1.5 mL) was then added over a 15 minute period to an ice cold solution of this compound (400 mg) in triethyl phosphite (25 mL). After stirring for 5 hours, the reaction mixture was poured over ice (25g) and stirred. The pH of the solution was adjusted to 7.5 by adding sodium bicarbonate, followed by extraction with ethyl acetate (4×25 mL). Organic layers were combined, dried over anhydrous $MgSO_4$ and evaporated. The residue was chromatographed over silica gel using 9:1 dichloromethane-methanol. The product thus isolated was treated with 70% trifluoroacetic acid for 20 mon. Volatiles were removed under high vacuum and the residue was redissolved in water (20 mL) and passed through a column of Amberlite (400), OH⁻ form. The column was eluted with water (3×25ml) and the effluents were discarded. Final elution was done with a solution of 0.5% tert-butylamine in water. Fractions containing the product were collected and evaporated under high vacuum and the residue was redissolved in distilled water (25 mL) and lyophilized until constant weight was attained. The title compound was obtained as a white solid. m.p. 130 C.

Synthesis of Pyrazolo Pyrimidines

Still another aspect of this invention is the preparation of 5'-substituted pyrazolo[3,4-d]pyrimidine ribosides. Accordingly, a substituted pyrazolo[3,4-d]pyrimidine is ribosylated with an esterified 5-hydroxy, 5-azido or 5-deoxyribofuranoside in the presence of a Lewis acid such as boron trifluoride. Browne et al., Ser. No. 07/812,916; Cottam, et al., *J. Med. Chem.*, 27:1120 (1984).

EXAMPLE 7

Preparation of Pyrazolo Pyrimidines

The 5-substituted ribofuranoside is prepared by esterification of the deblocked sugar. Suitable esters include the acetate, benzoate, toluate, anisoate and the like. The substituted pyrazolo[3,4-d]pyrimidine base may be prepared by a variety of known procedures which are apparent to practitioners.

One route comprises coupling an esterified ribose prepared as described above with a 3-substituted pyrazolo[3,4-d]pyrimidone-4-one. After ribosylation the pyrimidine riboside may be activated by chlorination with thionyl chloride/dimethylformamide or similar reagents and then reacted with ammonia or an amine to provide a variety of 5'-modified N4-substituted amino-pyrazolo[3,4-d]pyrimidine nucleosides. Another route for preparation of substituted pyrazolo[3,4-d]pyrimidine nucleosides comprises coupling the esterified ribose with various substituted 4-amino or 4-substituted aminopyrazolo[3,4-d]pyrimidines. The resulting products are then further modified or deblocked to afford the desired compounds. For example, 3-phenyl-4- phenylaminopyrazolo[3,4-d]pyrimidine 5'-modified ribosides are prepared from 3-phenyl-4-phenylaminopyrazolo[3,4-d]pyrimidine and various 5-modified sugars.

In another aspect of the present invention, 3-halogenated pyrazolo[3,4-d]pyrimidine ribosides can be arylated using arylboronic acids and palladium catalysts as described for the pyrrolo[2,3-d]pyrimidines. Thus, 3-iodopyrazolo[3,4-d] pyrimidone nucleosides are prepared by nonaqueous diazotization-iodination of the 3-amino compounds using a nitrite ester such as isoamyl nitrite and methylene iodide. Alternatively, 4-chloro or 4-amino pyrazolo(3,4-d) pyrimidine may be iodonated using N-iodosuccinide in a solvent such as DMF and the resulting 5-iodo heterocycle is coupled to the sugar to obtain the desired 4-iodonated pyrazolo(3,4-d)pyrimidine nucleoside.

Further modifications include reduction of the 5'-azido moiety to afford the 5'-amino compounds or the 5'-amides and urethanes as described above. Ester prodrugs ($C_1$ and $C_2$) of various 5'-amino nucleosides are prepared by reduction of the 5'-azide esters using previously described reagents.

EXAMPLE 8

Preferred Preparation of Pyrazolo Compounds

The general route for the synthesis of various 3-aryl-4-arylaminopyrazolo(3,4-d)pyrimidine nucleosides is delineated in Scheme 4. Various 3-aryl substituted 5-aminopyrazole-4-carbonitriles (17) are synthesized by a procedure analogous to the one reported in Kobayashi, Chem. Pharm. Bull. (Japan) 21, 941 (1973). These intermediates are further converted by a three step procedure to provide the heterocycles (18) used for synthesis of final compounds. Cheng, C. C., Robins, R. K., J. Org. Chem., 21, 1240 (1966).

lyxofuranoside, which can be treated with acetic anhydride in an acetic acid/sulfuric acid mixture at 0 C. to provide the desired sugar.

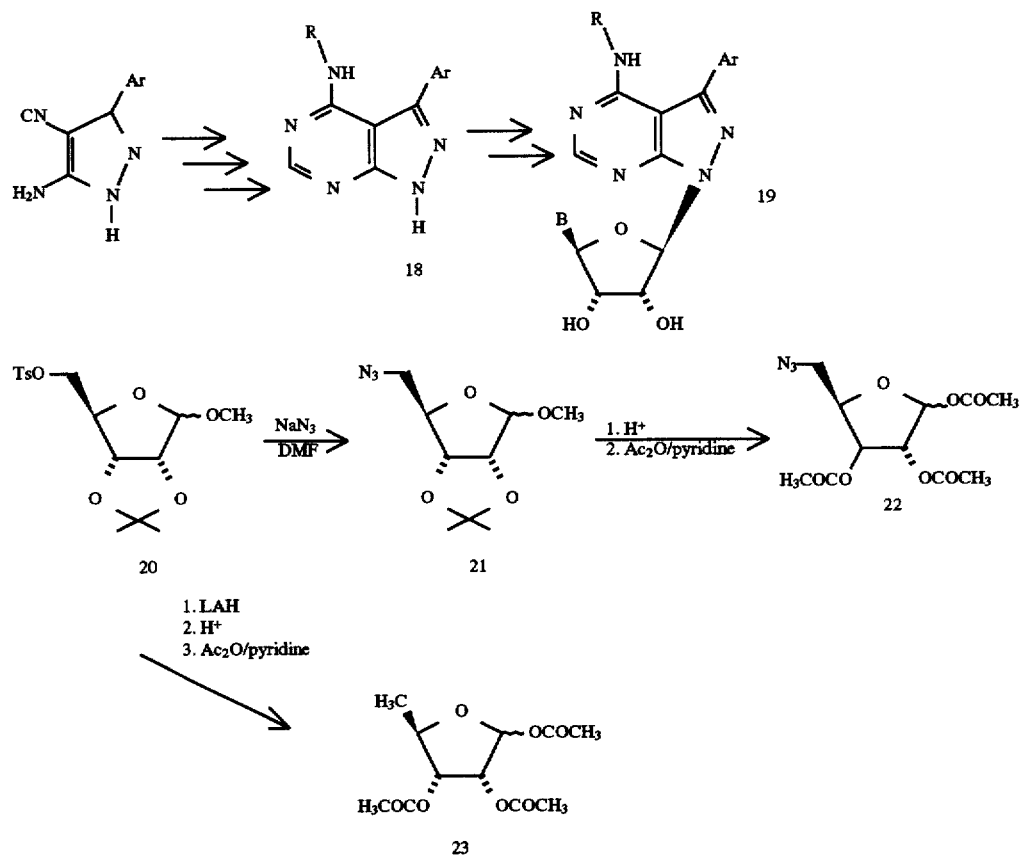

SCHEME 4

The carbohydrate moieties used in the current invention, e.g. 5-azido-5-deoxy-1,2,3-tri-O-acetyl-ribofuranose (22), where B=$CH_2N_3$ is synthesized as shown in Scheme 4. Treatment of (20) (Snyder et al., Carbohydrate Research, 163:169 (1987)) with sodium azide in dry DMF at elevated temperatures provided the corresponding 5-azido ribofuranoside (21) which is subjected to removal of the protecting groups under acidic conditions and the resulting 5-azido-5-deoxy-ribose is acetylated with acetic anhydride and pyridine to provide (22).

5-Deoxy-1,2,3-tri-O-acetyl-D-ribofuranose used in the current invention is synthesized by subjecting (23) to LAH reduction to provide methyl 5-deoxy-2,3-isopropylidene-D-ribofuranose (20) (Scheme 4). It was subjected to same protecting group manipulations as above to obtain (23) (where B=$CH_2H$). See, e.g. Formula 1 and Snyder et al., Carbohydrate Research, 163:169 (1987).

The intermediate 1 -O-acetyl-2,3,5-tri-O-benzoyl-L-lyxofuranoside used to synthesize the lyxose derivative of the invention can be made by treating L-lyxose (commercially available) with methanolic HCl at room temperature to provide 1-O-methyl-L-lyxofuranoside. This intermediate is then treated with benzoic anhydride in pyridine to provide methyl 2,3,5-O-tri-O-benzoyl-L-

Coupling of heterocycles with the above ribofuranose (or lyxofuranose) moieties can be conducted in boiling nitromethane using $BF_3$-etherate as a catalyst to obtain blocked nucleosides which upon deblocking with sodium methoxide in methanol provides the desired 5'-modified 3-aryl-4-arylaminopyrazolo(3,4-d)pyrimidine nucleosides of general structure (19).

The following examples can be synthesized by same procedure.

52) 3-(4-N,N-Dimethylaminoethylphenyl)-4-N-(4-fluoropheny)amino-1-(5- deoxy-β-D-ribofuranosyl) pyrazolo(3,4-d)pyrimidine.

53) 3-(4-N,N-Diethylaminomethylphenyl)-4-N-(4-fluorophenyl)amino-1-(5- deoxy-β-D-ribofuranosyl) pyrazolo(3,4-d)pyrimidine.

54) 3-(4-N,N-Dimethylaminoethylphenyl)-4-N-(4-fluorophenyl)amino-1-(5- deoxy-β-D-ribofuranosyl) pyrazolo(3,4-d)pyrimidine.

55) 3-(4-Morpholinomethylphenyl)-4-N-(4-fluorophenyl)amino-1-(5-deoxy-β-D- ribofuranosyl) pyrazolo(3,4-d)pyrimidine.

56) 3-(4-Morpholinoethylphenyl)-4-N-(4-fluorophenyl) amino-1-(5-deoxy-β-D- ribofuranosyl)pyrazolo(3,4-d) pyrimidine.

57) 3-(1-Piperidinomethylphenyl)-4-N-(4-fluorophenyl) amino-1-(5-deoxy-β-D- ribofuranosyl)pyrazolo(3,4-d) pyrimidine.

58) 3-(1-Piperidinoethylphenyl)-4-N-(4-fluorophenyl) amino-1-(5-deoxy-β-D- ribofuranosyl)pyrazolo(3,4-d) pyrimidine.

59) 4-N-(1-Piperizinomethylphenyl)amino-3-phenyl-1-(5-deoxy-β-D- ribofuranosyl)pyrazolo(3,4-d) pyrimidine.

60) 3-(1-Piperizinoethylphenyl)-4-N-(4-fluorophenyl) amino-1-(5-deoxy-β-D- ribofuranosyl)pyrazolo(3,4-d) pyrimidine.

61) 3-(4-Trifluoroacetamidophenyl)-4-N-(4-fluorophenyl)amino-1-(5-deoxy-β- D-ribofuranosyl) pyrazolo(3,4-d)pyrimidine.

62) 3-(4-Trifluoroacetylaminosulfonylphenyl)-4-N-(4-fluorophenyl)amino-1-(5- deoxy-β-D-ribofuranosyl) pyrazolo(3,4-d)pyrimidine.

63) 3-(4-N-Guanidinophenyl)-4-N-(4-fluorophenyl) amino-1-(5-deoxy-β-D- ribofuranosyl)pyrazolo(3,4-d) pyrimidine.

64) 3-(4-C-Amidinophenyl)-4-N-(4-fluorophenyl)amino-1-(5-deoxy-β-D- ribofuranosyl)pyrazolo(3,4-d) pyrimidine.

65) 3-(4-Carboxyphenyl)-4-N-(4-fluorophenyl)amino-1-(5-deoxy-β-D- ribofuranosyl)pyrazolo(3,4-d) pyrimidine.

Lyxose analogs can also be prepared, for example:

66) 3-(4-N,N-Dimethyaminomethylphenyl)-4-N-(4-fluorophenyl)amino-1-(1-α- L-lyxofuranosyl)pyrazolo (3,4-d)pyrimidine.

67) 3-(4-N,N-Dimethyaminoethylphenyl)-4-N-(4-fluoropheny)amino-1-(1-α-L- lyxofyranosyl)pyrazolo (3,4-d)pyrimidine.

68) 3-(4-N,N-Diethylaminomethylphenyl)-4-N-(4-fluorophenyl)amino-1-(1-α-L- lyxofyranosyl)pyrazolo (3,4-d)pyrimidine.

69) 3-(4-N,N-Dimethyaminoethylphenyl)-4-N-(4-fluorophenyl)amino-1-(1-α-L- lyxofyranosyl)pyrazolo (3,4-d)pyrimidine.

70) 3-(4-Morpholinomethylphenyl)-4-N-(4-fluorophenyl)amino-1-(1-α-L- lyxofyranosyl)pyrazolo (3,4-d)pyrimidine.

71) 3-(4-Morpholinoethylphenyl)-4-N-(4-fluorophenyl) amino-1-(1-α-L- lyxofyranosyl)pyrazolo(3,4-d) pyrimidine.

72) 3-(1-Piperidinomethylphenyl)-4-N-(4-fluorophenyl) amino-1-(1-α-L- lyxofyranosyl)pyrazolo(3,4-d) pyrimidine.

73) 3-(1-Piperidinoethylphenyl)-4-N-(4-fluorophenyl) amino-1-(1-α-L- lyxofyranosyl)pyrazolo(3,4-d) pyrimidine.

74) 4-N-(1-Piperizinomethylphenyl)amino-3-phenyl-1-(1-α-L- lyxofyranosyl)pyrazolo(3,4-d)pyrimidine.

75) 3-(1-Piperizinoethylphenyl)-4-N-(4-fluorophenyl) amino-1-(1-α-L- lyxofyranosyl)pyrazolo(3,4-d) pyrimidine.

76) 3-(4-Trifluoroacetamidophenyl)-4-N-(4-fluorophenyl)amino-1-(1-α-L- lyxofyranosyl)pyrazolo (3,4-d)pyrimidine.

77) 3-(4-Trifluoroacetylaminosulfonylphenyl)-4-N-(4-fluorophenyl)amino-1-(1- α-L-lyxofyranosyl)pyrazolo (3,4-d)pyrimidine.

78) 3-(4-N-Guanidinophenyl)-4-N-(4-fluorophenyl) amino-1-(1-α-L- lyxofyranosyl)pyrazolo(3,4-d) pyrimidine.

79) 3-(4-C-Amidinophenyl)-4-N-(4-fluorophenyl)amino-1-(1-α-L- lyxofyranosyl)pyrazolo(3,4-d)pyrimidine.

80) 3-(4-Carboxyphenyl)-4-N-(4-fluorophenyl)amino-1-(1-α-L- lyxofyranosyl)pyrazolo(3,4-d)pyrimidine.

EXAMPLE 9

Synthesis of Heterocycles

Heterocycles made according to this example were used in the previous example (Scheme 4). The following heterocycles, used as starting materials in this example, were made by procedures analogous to those in Kobayashi, *Chem. Pharm. Bull.* (Japan), (1973), 21, 941 (1973) and Cheng, et al. *J. Org. Chem.*, 21, 1240 (1966).

Pyrazolo(3,4-d)pyrimidine heterocycles synthesized by the above procedure 1. 4-N-(N,N-Dimethylaminomethylphenyl)amino-3-phenylpyrazolo(3,4-d)pyrimidine
2. 4-N-(N,N-Diethylaminomethylphenyl)amino-3-phenylpyrazolo(3,4-d)pyrimidine
3. 4-N-(N,N-Diethylaminoethylphenyl)amino-3-phenylpyrazolo(3,4-d)pyrimidine
4. 4-N-(N,N-Dimethylaminoethylphenyl)amino-3-phenylpyrazolo(3,4-d)pyrimidine
5. 4-N-(N,N-Diethylaminoethyleneaminophenyl)amino-3-phenylpyrazolo(3,4-d)pyrimidine
6. 4-N-(2-(1-piperazino) ethylphenyl)amino-3-phenylpyrazolo(3,4-d)pyrimidine
7. 4-N-(2-(1-Piperidino)ethylphenyl)amino-3-phenylpyrazolo(3,4-d)pyrimidine
8. 4-N-(2-(4-Morpholino)ethylphenyl)amino-3-phenylpyrazolo(3,4-d)pyrimidine
9. 4-N-(4-Cyanophenyl)amino-3-phenylpyrazolo(3,4-d) pyrimidine
10. 3-(N,N-Dimethylaminomethylphenyl)-4-N(4-fluorophenyl)aminopyrazolo(3,4-d)pyrimidine
11. 3-(N,N-Diethylaminomethylphenyl)-4-N-(4-fluorophenyl)aminopyrazolo(3,4-d)pyrimidine
12. 3-N-(N,N-Diethylaminoethylphenyl)-4-N-(4-fluorophenyl)aminopyrazolo(3,4-d)pyrimidine
13. 3-(N,N-Dimethylaminoethylphenyl)-4-N-(4-fluorophenyl)aminopyrazolo(3,4-d)pyrimidine
14. 3-(N,N-Diethylaminoethyleneaminophenyl)-4-N-4-fluorophenyl)aminopyrazolo(3,4-d)pyrimidine
15. 3-(2-(1-piperazino)ethylphenyl)-4-N-(4-fluorophenyl) aminopyrazolo(3,4-d)pyrimidine.

A. Preparation of 5-Azido-5-deoxy-1-O-methyl-2,3-O-(1-methylethylidene)-D-ribofuranoside (21).

A mixture of 1-O-methyl-2,3-O-(1-methylethylidene)-5-O-(4-methylbenzenesulfonyl)-D-ribofuranoside (20) (8.0 g), dry DMF (40 mL) and NaN$_3$ (4.0 g) was heated at 80 C. for 12 hours. The solvent was evaporated and the residue was chromatographed over silica gel using CH$_2$Cl$_2$. The fractions containing the faster moving product were pooled and evaporated to obtain 4.8 g (94% yield) of a syrupy product.

B. Preparation of 5-azido-5-deoxy-1,2,3-O-Triacetyl-D-ribofuranoside (22)

A solution of 5-azido-5-deoxy-1-O-methyl-2,3-O-(1-methylethylidene)-D-ribofuranoside (21), 4.6 g, 20 mmol in 0.1% H$_2$SO$_4$ (300 mL) was refluxed for 3 hours. The acid was neutralized (pH ~5) with Amberlite 400 (OH⁻ form) and the resin filtered and washed with ethanol (2×20 mL). The filtrate was evaporated to dryness under high vacuum to give the title compound as a syrupy residue; $^1$H and $^{13}$C NMR confirmed the identity of the product as a mixture of α and β anomers. This product(3.1 g, 0.017 mole) was dissolved in 10 ml of pyridine and was treated with acetic anhydride (18 ml). The mixture stirred for 24 hours and concentrated under vacuum. The residue was dissolved in $CH_2Cl_2$ and the solution washed with 5% $NaHC_3O$. The organic layer was then washed with 0.5N $H_2SO_4$, dried ($Na_2SO_4$) and evaporated. The residue was filtered through a plug of silica gel ($CH_2Cl_2$) and the filtrate concentrated to afford the title compound, 4.5 g (98% yield) as a semisolid mixture of α and β isomers.

C. Preparation of 5-deoxy-1,2,3-tri-O-acetyl-D-ribofuranoside (23)

This compound was prepared as described in Snyder, J.; Serianni, A.; *Carbohydrate Research*, 163:169 (1987).

D. Synthesis of 3-aryl-4-arylaminopyrazolo(3,4-d) pyrimidine nucleosides (19)

To a slurry of the heterocycle (18) (5.0 mmol) in nitromethane under argon, was added acyl protected ribofuranose(5–7 mmol). The mixture was heated approximately to 80° C. and treated with $BF_3$-etherate(7.0 mmol). The reaction mixture was refluxed gently for 90 minutes, then cooled and evaporated under vacuum. The residue was treated with triethyl amine and water and extracted with methylene chloride. The organic layer was dried over sodium sulfate and evaporated. The residue was chromatographed over silica gel using gradient of ethyl acetate and hexane as eluting system. The product thus obtained was dissolved in methanol and treated with freshly prepared sodium methoxide solution to adjust the pH to ~10. After stirring the reaction for 2 hours the pH of the solution was adjusted to 4 by adding strongly acidic resin Dowex-120 H$^+$ type. The resin was filtered off, washed with methanol and the filtrate was evaporated under reduced pressure. The residue was crystallized from appropriate solvent. It will be readily apparent that many compounds, including those in Formula 1 above, and in the appended claims, can be made by these various exemplary methods.

EXAMPLE 10

Representative Preferred Pyrrolo[2,3-d]Pyrimidines

Representative, preferred pyrrolo[2,3-d]pyrimidine compounds of the invention, which are not limiting, are identified below. Generally, the most preferred compounds have two aryl groups (e.g. phenyl or substituted phenyl) at positions D and W of the formula below (W corresponds to $(CH_2)_pX$ of Formula 1 ). Particularly preferred are compounds where D is phenyl, $A_1$, $A_2$, G and E of Formula 1 are all hydrogen, and B of Formula 1 is methyl. B may also be $CH_2OH$, and in that case a particularly preferred compound is 81) 4-N-(4-N,N-dimethylaminomethylphenyl)amino-5-phenyl-7-(1 -β-D- ribofuranosyl)pyrrolo[2,3-d] pyrimidine.

Thus, particularly preferred pyrrolo pyrimidines of the invention can be represented by the following formula:

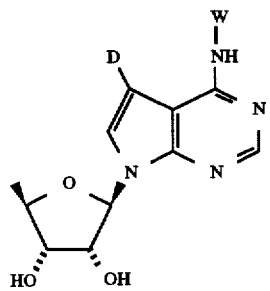

where D is most preferably (a) phenyl, or is preferably (b) 3-pyridyl, (c) 4-(1-morpholinomethyl)phenyl, (d) 4-(1-piperidinoethyl)phenyl, (e) 4-(1-piperizinoethyl)phenyl, (f) 4-(2-aminoethyl)phenyl, (g) 4-(N,N-dimethylaminomethyl) phenyl, (h) 4-(N,N-diethylaminomethyl)phenyl, or (I) 4-(N,N-diethylaminoethyl)phenyl.

When D is phenyl, preferred compounds are those where W is:

82) 4-((Methylphosphoryl)oxy)phenyl
83) phenyl
84) (4-(2-Aminoethyl)phenyl
85) 4-(1-morpholino-2-ethylphenyl)
86) 4-(N-Acetylaminosulfonyl)phenyl
87) 4-(1-piperazinoethyl)phenyl
88) 4-N, N-Dimethylaminomethylphenyl
89) 4-(diethylaminoethyleneaminoethyl)phenyl
90) 4-(2-diethylaminoethyl)phenyl)
91) 4-(2-dimethylaminoethyl)phenyl
92) 4-N-Trifluoromethanesulfonylaminophenyl
93) (4-amidoxime)phenyl
94) 4-phosphatephenyl
95) 4-N-aminoamidinophenyl
96) 4-N-aminoguanidinophenyl
97) 4-carboxymethyloxyphenyl
98) 4-(2-aminoethyl)carboxamidophenyl
99) 4-(2-N,N-diethylaminoethyl)carboxamidophenyl
100) 4-(morpholinoethyl)carboxamidophenyl
101) 4-(1-pyperazinoethyl)carboxamidophenyl
102) 4-(pyperidinoethyl)carboxamidophenyl
103) 4-(N-ethylaminomethyl)phenyl
104) 4-(N-methylaminomethyl)phenyl
105) 3-(N,N-dimethylaminomethyl)phenyl
106) 4-(N,N-dimethylaminomethyl)phenyl
107) 3-(N,N-diethylaminomethyl)phenyl
108) 4-(N,N-diethylaminomethyl)phenyl
109) 3-(N,N-dimethylaminoethyl)phenyl
110) 3-(N,N-diethylaminoethyl)phenyl
111) 4-(N,N-diethylaminoethyl)phenyl
112) 3-(N,N-diethylaminopropyl)phenyl
113) 4-hydroxypropylphenyl
114) 4-(3-aminopropyl)phenyl
115) 4-(N,N-diethylaminopropyl)phenyl
116) 3-(1-piperidinomethyl)phenyl
117) 4-(N-trifluoromethanesulfonamido)phenyl
118) 4-N-fluorosulfonylaminophenyl When D is 3-pyridyl, preferred compound are those where W is:

119) phenyl
120) 4-fluorophenyl
121) 2-pyridinomethyl; or
122) 4-dimethylaminomethylphenyl.

When D is any of the groups (c)–(l) immediately above, then W is preferably fluorophenyl (Examples 124–130, respectively).

Other preferred pyrrolo pyrimidine compounds of the invention are those where D is iodo, and especially preferred compounds of this kind are those where W is 41) 2-pyridylmethyl (see also #46)
42) 4-pyridylmethyl
43) 2-pyridylethyl
44) 3-pyridylmethyl
45) 2-benzimidazolylmethyl
131) 2-thiophenylmethyl If desired, the compounds of the invention can be provided as salts, e.g. hydrochloride salts, such as 4-(2-pyridylmethylamino)-5-iodo-7-(5-deoxy-1-β-D-ribofuranosyl)pyrrolo[2,3-d]pyrimidine hydrochloride (Examples 41 and 46). Compounds having a lyxose sugar moiety, in place of ribose, can also be provided. As one example, the following compounds, corresponding to Examples 41 and 42 are within the scope of the invention:

132) 4-N-(2-pyridylmethylamino)-5-iodo-7-(1-α-L-lyxofuranosyl)pyrrolo[2,3-d]pyrimidine; and
133) 4-N-(4-pyridylmethylamino)-5-iodo-7-(1-α-L-lyxofuranosyl)pyrrolo[2,3-d]pyrimidine.

EXAMPLE 11

Preferred Pyrazolo[3,4-d]Pyrimidines

Representative, preferred pyrazolo[3,4-d] pyrimidine compounds of the invention, which are not limiting, are identified below. Generally, the most preferred compounds have two aryl groups (e.g. phenyl or substituted phenyl) at positions D and W of the formula below (W corresponds to $(CH_2)_nX$ of Formula 1). Particularly preferred are compounds where D is phenyl. $A_1$, $A_2$, and G of Formula 1 are all hydrogen, and B of is methyl. B may also be $CH_2OH$, and in that case a preferred compound is 134) 1-(1-β-D-ribofuranosyl)-3-phenyl-4-N-(4-N,N-dimethylaminomethyl)phenylaminopyazolo[3,4-d] pyrimidine.

Thus, preferred pyrazolo pyrimidines can be represented by the formula:

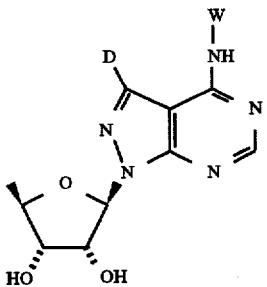

where D is most preferably (a) phenyl, or is preferably (b) 3-pyridyl, (c) 4-(1-morpholinomethyl)phenyl, (d) 4-(1-piperidinoethyl)phenyl, (e) 4-(1-piperizinoethyl)phenyl, (f) 4-(2-aminoethyl)phenyl, (g) 4-(N,N-dimethylaminomethyl) phenyl, (h) 4-(N,N-diethylaminomethyl)phenyl, or (I) 4-(N, N-diethylaminoethyl)phenyl.

When D is phenyl, preferred compounds are those where W is:

135) 4-((Methylphosphoryl)oxy)phenyl
136) [4-(2-Aminoethyl)phenyl
137) 4-(1-morpholino-2-ethylphenyl)
138) (4-(N-Acetylaminosulfonyl)phenyl
139) 4-(1-piperazinoethyl)phenyl
140) 4-(N,N-dimethylaminomethylphenyl
141) 4-(N,N-diethylaminoethyleneaminoethyl)phenyl
142) 4-(2-diethylaminoethyl)phenyl
143) 4-(2-dimethylaminoethyl)phenyl
144) 4-N-Trifluoromethanesulfonylaminophenyl
145) (4-amidoxime) phenyl
146) 4-(N,N-dimethylaminomethyl)phenyl
147) 4-phosphatephenyl
148) 4-N-aminoamidinophenyl
149) 4-N-aminoguanidinophenyl
150) 4-carboxymethyloxyphenyl
151) 4-(2-aminoethyl)carboxamidophenyl
152) 4-(2-N, N-diethylaminoethyl)carboxamidophenyl
153) 4-(morpholinoethyl)carboxamidophenyl
154) 4-(1-pyperazinoethyl)carboxamidophenyl
155) 4-(pyperidinoethyl)carboxamidophenyl
156) 4- N-ethylaminomethyl)phenyl
157) 4-(N-methyl-N-aminomethyl)phenyl
159) 4-(N,N-dimethylaminomethyl)phenyl
160) 3-(N,N-diethylaminomethyl)phenyl
161) 4-(N,N-diethylaminoethyl)phenyl
162) 4-(3-aminopropyl)phenyl
163) 4-(N,N-diethylaminopropyl)phenyl
164) 3-(1-piperidinomethyl)phenyl
165) 4-(N-trifluoromethanesulfonamido)phenyl
166) 4-N-fluorosulfonylaminophenyl When D is 3-pyridyl, preferred compound are those where W is:

167) phenyl
168) 4-fluorophenyl
169) 2-pyridinomethyl; or
170) 4-N,N-dimethylaminomethylphenyl.

When D is any of the groups (c)–(l) immediately above, then W is preferably fluorophenyl (Examples 177–183, respectively).

If desired, these compounds can be provided as salts, e.g. hydrochloride salts, or in lyxose form, as described in Example 10.

Utility

The adenosine kinase inhibitors of the present invention may be used in the treatment of a variety of clinical situations where increasing local levels of adenosine are beneficial. The compounds of the invention act as potent inhibitors of adenosine kinase in vitro, and may be readily administered intravenously.

Adenosine has been proposed to serve as a natural anticonvulsant. Compounds of the present invention which enhance adenosine levels are useful in seizure disorders, as shown in animal models of seizures detailed below. Adenosine kinase inhibitors may be used in the treatment of patients with seizures or epilepsy or patients who might have chronic low or insufficient adenosine levels or might benefit from increased adenosine such as those suffering from autism, cerebral palsy, insomnia or other neuropsychiatric symptoms.

Adenosine kinase inhibitors of the invention find further utility in the treatment of acute pain, including but not limited to peri-operative, post-surgical, and end-stage cancer pain. Compounds of the invention are also useful in controlling chronic pain, including but not limited to pain caused by arthritis, cancer, trigeminal neuralgia, multiple sclerosis, neuropathies such as those arising from diabetes and AIDS and in addition, lower back pain and phantom limb pain. Treatment of acute and chronic pain can be treated by administration of the compounds of the invention in a systemic or oral fashion, as illustrated by animal models detailed below.

Adenosine has been reported to be an endogenous modulator of inflammation by virtue of its effects on stimulated neutrophil function and on macrophage, lymphocyte and platelet function. The compounds of this invention may therefore be used in treating conditions in which inflammatory processes are prevalent such as arthritis, reperfusion injury, and other inflammatory disorders.

The compounds of the invention are also useful in the treatment of chronic neurodegenerative disease, such as Alzheimer's disease, Parkinson's deisease, ALS, Huntington's disease, and AIDS dimentia.

Stroke and central nervous system ("CNS") trauma are conditions where tissue injury results from reduced blood supply to the CNS and are thus amenable to an intervention that provides increased levels of adenosine to the compromised tissue. It is reported that a significant component of the neurodegeneration resulting from stroke or CNS trauma is caused by increased excitatory amino acid release and sensitivity, which results in neurons being stimulated to death. In addition to vasodilatory properties, adenosine has been reported to inhibit release of excitatory amino acids (Burke and Nadler *J. Neurochem.*, 51:1541 (1988)) and responsiveness of neurons to excitation. The compounds of this invention, which increase adenosine levels, may also be used in the treatment of conditions where release of or sensitivity to excitatory amino acids is implicated.

To assist in understanding the present inventions and especially their properties and utilities, the results of a series of experiments are also included. These experiments demonstrated that a number of compounds of the present invention were potent inhibitors of a purified cardiac adenosine kinase. Certain adenosine kinase inhibitors were found to inhibit seizures in a well-established animal model, and exemplary compounds inhibited pain in two other animal models. Results are set forth in Tables 1–3.

AK Inhibition

Adenosine kinase activity was measured essentially as described by Yamada et al *Biochim. Biophys. Acta* 660, 36–43 (1988) with a few minor modifications. Assay mixtures contained 50 mM TRIS-maleate buffer, pH 7.0, 0.1% BSA, 1 mM ATP 1 mM $MgCl_2$, 0.5 μM [U-$^{14}$C] adenosine (400–600 mCi/mmol) and varying duplicate concentrations of inhibitor. The reactions were initiated by addition of approximately 0.1 μU partially purified pig heart adenosine kinase, where one unit is defined as that amount of enzyme required to phosphorylate 1 μmol adenosine per minute. The reactions were incubated for 20 minutes at 37° C. The assay was quenched upon spotting 30 μL aliquots onto 2 cm² pieces of Whatman DE81 anion exchange paper. The paper squares were washed for 3 minutes in 6 L distilled/deionized water to remove the unreacted adenosine. The washed squares were rinsed in 95% ethanol and dried in an oven at 100° C. for 10 minutes. The amount of $^{14}$C-AMP was quantified by scintillation counting. The concentration of inhibitor required to inhibit 50% of the adenosine kinase activity ($IC_{50}$) was determined graphically. The results for representative compounds of the invention are shown in Table 1.

Anticonvulsant Activity

The anticonvulsant activity of the tested compounds was evaluated in male SA rats (100–150 g, Simonsen) using the maximal electroshock (MES) model described in Swinyard et al., *Antiepileptic Drugs*, 3d Ed. at 85–102 (Levy, et al., eds.), N.Y.: Raven Press (1989). The rats were maintained on a 12/12 light/dark cycle in temperature controlled facilities with free access to food and water. For p.o. administration, the animals are fasted overnight, prior to the experiment. One hour prior to seizure testing, the animals were injected interperitoneally (ip) or orally (per os, pc) with one of various doses of test compound dissolved in DMSO or PEG 400.

Maximal electroshock seizures (MES) were induced by administering a 150 mA, 60 Hz current for 0.2 seconds via corneal electrodes using a Wahlquist Model H stimulator. The endpoint measurement was suppression of hind limb tonic extension (HTE), which was judged to occur when any hind leg extension did not exceed a 90 degree angle with the plane of the body. HTE suppression of this kind indicates that the test compound has the ability to inhibit seizures, in theory by inhibiting seizure propagation and spread, if not by raising the seizure threshold (i.e. preventing seizure potential). This endpoint was expressed as the percentage of animals in which the response was inhibited. Typically, compounds were screened initially at one hour following a dose of 5 mg/kg ip. In some cases, the effective dose at which 50% of the rats were protected ($ED_{50}$) was calculated from a dose response curve. The results for exemplary compounds of the invention are set forth in Table 1, expressed as $ED_{50}$ values. For compounds where the $ED_{50}$ was not calculated, the result is listed as >5 if HTE was inhibited in fewer than 50% of the animals in the initial screen, or <5 if HTE was inhibited in more than 50% of the animals in the initial screen. Results are shown in Table 1.

TABLE 1

| UTILITY OF REPRESENTATIVE AK INHIBITORS | | |
|---|---|---|
| | AK Inhibition | Anticonvulsant $ED_{50}$(MES) mg/kg |
| # | ($IC_{50}$) nmol. | ip | po |
| 1 | 4 | 5 | >20 |
| 22 | 2 | | |
| 3 | 2 | | >40 |
| 4 | 1 | >5 | |
| 6 | 1 | >5 | |
| 5 | 1 | 5 | |
| 7 | 1 | >5 | |
| 8 | 50 | >5 | |
| 40 | 3000 | >5 | |
| 42 | 75 | 2.0 | |
| 49 | 67 | 10.9 | 40 |
| 50 | 5 | 5 | |
| 41 | 70 | 0.5 | |
| 43 | 10,000* | 1.0 | |
| 44 | 120 | <5.0 | |
| 48 | 300 | | |

TABLE 1-continued

UTILITY OF REPRESENTATIVE AK INHIBITORS

| | AK Inhibition | Anticonvulsant $ED_{50}(MES)$ mg/kg | |
|---|---|---|---|
| # | ($IC_{50}$) nmol. | ip | po |
| 47 | 55 | | |
| 45 | 500 | | |
| 46 | 220 | | >5.0 |
| 37 | 5 | | >5 |

*This compound is a weak AK inhibitor in vitro, but has been shown by HPLC analysis of plasma to undergo metabolism in mice after oral administration (10 mg/kg) to generate a potent AK inhibitor.

Analgesic Activity

Analgesic activity of representative compounds of the invention was evaluated in male SA rats (100–150 g, Simonsen) using the hot plate and tail flick models of pain, similar to those described in Sosnowski et al., *J. Pharmacol. Exper. Ther.*, 250:3, 915–922 (1989). See also, *Life Sciences* 51:171–76 (1992). These models measure pain avoidance and tolerance in response to a regulated stimulus, and compare the response of animals before and after they are given test compound.

The tail flick response is evoked by placing the tail of a rat over a focused beam of light. The latency or response time to flick the tail away from the incident heat source was recorded electronically by an appropriate measuring device, for example an apparatus manufactured by Ugo Baslie. Longer times indicate greater tolerance to the thermally induced pain stimulus. The maximum exposure time is limited to avoid tissue damage (8 seconds), in the event a rat does not respond to the stimulus within a predetermined period. In this experiment, the rats were accommodated to the hand restraint of the testing to prevent spurious movements from causing false responses. A mark was made on the dorsal surface of each tail approximately 3–5 cm from the tip to ensure testing at the same location on the tail.

In the hot plate model, a rat is placed on a heated metal plate (typically 50 C.). The endpoint of this evaluation is the time required for the rat to lick its hind paw. A predetermined cutoff time (60 seconds) is used to protect the animals from injury, in the event there is no response. Three tests were performed 15 minutes apart prior to dosing; these tests serve as the baseline for each animal. Rats were gavaged with one of the various doses and the tail flick and hot plate responses were monitored at various times, e.g. 30, 60, 120,240, and 480 minutes after gavage.

Dose response curves for each compound in the tail flick and hot plate tests are made by plotting the dose against the normalized peak response, or maximum possible effect (MPE). The MPE is calculated as (test latency—baseline latency)×100%

(cutoff latency—baseline latency).

The effective dose at which 50% of the rats were protected ($ED_{50}$) was calculated from the dose response curve using linear regression analysis. Results for representative compounds according to the invention are set forth in Table 2.

Anti-Inflammatory Activity

Carrageenan (Type λ) was suspended in sterile PBS at 1% (w/v), autoclaved for 30 minutes, and stored at room temperature. Rats were pretreated with vehicle or AK inhibitor (10 mg/kg) by oral gavage or i.p. administration and the volume of the left hind paw was measured using a water displacement plethysmometer (Stoelting Co., Wood Dale, Ill.). One hour after oral treatment or 30 minutes after i.p. treatment, the rats were briefly anesthetized, and 0.1 ml of the carrageenan solution was injected subcutaneously into the planar surface of the left hind paw. The ensuing paw swelling was measured by plethysmometry after 3 hours. The paw volume in millileters was subtracted from the pre-injection paw volume. Data are presented as the percent inhibition of paw swelling in AK inhibitor treated animals, compared to vehicle treated control animals. Rosengren et al., *J. Immunology* 154:5444–51 (1995).

TABLE 2

ANALGESIC/ANTI-INFLAMMATORY UTILITY

| | Analgesic $ED_{50}$ (mg/kg) | | | | Carrageenan Paw (% inhibition) | |
|---|---|---|---|---|---|---|
| | Hot Plate | | Tail Flick | | | |
| # | ip | po | ip | po | ip | po |
| 1 | 15.2 | | 15 | | 26.0 | 19.2 |
| 22 | | | | | 31.6 | 12.4 |
| 3 | | | | | | |
| 4 | | | | | 39.9 | 2.5 |
| 6 | | | | | | |
| 5 | | | | | −3.4 | 4.1 |
| 7 | | | | | 19.0 | 7.7 |
| 8 | | | | | | |
| 40 | | | | | | |
| 42 | | | | | | |
| 49 | | | | | | |
| 50 | | | | | | |
| 41 | 1.2 | | <1.0 | | 84.8 | 90.6 |
| 43 | | | | | 58.6 | 69.7 |
| 44 | | | | | | |
| 48 | | | | | | |
| 47 | | | | | −4.4 | 9.8 |
| 45 | | | | | | |
| 41 | | | | | | |
| 37 | | | | | | |

Water Solubility

Water solubility was estimated by taking a sample of the compound to be tested (usually between 1 and 2 mg) and adding 1.0 ml of deionized water or an aqueous buffer solution. The sample was sonicated for a period of up to 20 minutes. If a solution was not obtained, further solvent was added and the process was repeated until a clear solution was obtained, and the results were recorded. Solutions used were 50 mM potassium biphthalate (pH 4); 100 mM glycine (pH 9); 25 mM sodium carbonate and 25 mM sodium bicarbonate (pH 10); or deionized water (DI). The solubilities for representative compounds of the invention are shown in Table 3.

TABLE 3

WATER SOLUBILITY

| | Water Solubility | |
|---|---|---|
| # | mg/ml | pH |
| 1 | >5 | DI |
| 22 | >1 | 4 |
| 3 | >1 | 4 |
| 4 | >1 | 4 |
| 6 | >1 | 4 |

TABLE 3-continued

WATER SOLUBILITY

| # | Water Solubility mg/ml | pH |
|---|---|---|
| 5 | >5 | DI |
| 7 | >1 | 4 |
| 8 | >1 | 10 |
| 40 | >1 | 9 |

For comparison, a representative compound without the water solubilizing groups of the invention, 5-phenyl-4-N-phenylamino-7-(5-deoxy-1-β-D-ribofuranosyl)pyrrolo[2,3-d]pyrimidine, has a water solubility of less than 20 μg/ml at a suitable pH for i.v. administration (e.g. pH 4 to 10).

Liver Toxicity Assay

Female SA rats (150–200 g) are anesthetized with halothane and cannulated via the internal jugular vein. The animals are allowed to recover for 3 days. At this time, 37.5 μmole/kg of an AK inhibitor is dissolved in 50% PEG400 and infused through the jugular catheter over 20 minutes. Twelve hours later, an additional 37.5 μmole/kg is infused over 20 minutes (total dose=75 μmole/kg). Twelve hours after the second dose, the animals are anesthetized with halothane and exsanguinated through the inferior vena cava. Liver enzymes (serum glutamic-oxaloacetic transaminase (SGOT), serum glutamic-pyruvic transaminase (SGPT), alkaline phosphatase) and total bilirubin in the serum samples are determined by a commercial laboratory.

TABLE 4

LIVER TOXICITY

| # | Total Bilirubin (mg/dL) | SGOT (IU/L) | SGPT (IU/L) | Alkaline (IU/L) Phosphatase |
|---|---|---|---|---|
| Vehicle | 0.10 ±0.04 | 59 ±3 | 42 ±0 | 140 ±50 |
| REF. A | 0.76 | 508 | 76 | 163 |
| REF. B | 0.30 | 100 | 41 | 113 |
| 1 | 0.08 | 51 | 20 | 96 |
| 22 | 0.13 | 95 | 38 | 128 |
| 4 | 1.03 | 388 | 70 | 93 |

REF A. 4-amino-5-iodo-7-(5-deoxy-1-β-D-ribofuranosylpyrrolo[2,3-d] pyrimidine
REF B. 4-amino-1-(5-amino-5-deoxy-1-β-D-ribofuranosyl)-3-bromopyrazolo[3,4-d]pyrimidine HCL

Prodrugs

Prodrugs of the described compounds are within the scope of the invention, and can be prepared by esterification of the hydroxyl groups on the ribofuranose ring. Specially preferred will be the ester derivatives that improve the water solubility properties of the resulting prodrug in order to facilitate their administration via iv route. Examples of prodrugs within the scope of the invention are illustrated below.

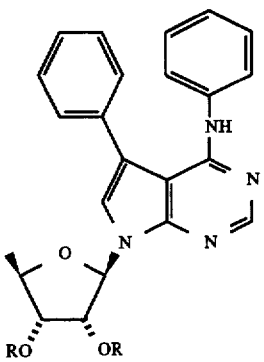

where R is selected from the group consisting of:

an ester of an alkanoic acid, such as an acetate, propionate, or any other alkyl carboxylate;

an ester of an aminoacid such as a valine, glycine; a carbonate, such as a cyclic 2',3'-carbonate or a dicarbonate;

a phosphate ester, including but not limited to cyclic 2',3'-phosphate;

an ester of a functionalized alkanoic acid where the substituent on the alkyl chain is a substituted amine having the formula

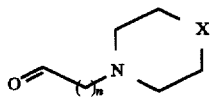

where n is 3 to 5 and X=O, NH, NHCH$_3$, NHCH$_2$CH$_3$;

an ester of a functionalized alkanoic acids where the substituent on the alkyl chain is a substituted amide of the formula

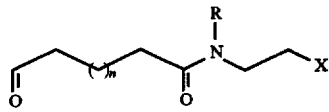

where n=2–4; R=CH$_3$, CH$_2$CH$_3$; X=SO$_3$Na, PO(ONa)$_2$, NR$^1$R$^2$, with R$^1$ and R$^2$=alkyl or aminoalkyl groups;

benzoate esters substituted with solubilizing groups at the 3- or 4- position of the aromatic ring as illustrated below:

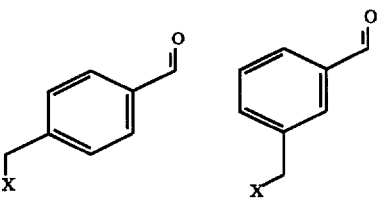

where X=NR$^1$R$^2$, with R$^1$ and R$^2$=methyl, ethyl or propyl
X=4-morpholino, 1-piperazino, 4-methyl-1-piperazino, 1-piperidino;

an ester of a heteroaromatic carboxylic acid such as 2-pyridinocarboxylic acid, 3-pyridino carboxylic acid, 4-pyridino carboxylic acid, N-substituted 2- or 3-pyrrolocarboxylic acid; or an ester of ionized carboxylic acid, e.g. N-methyl pyridinium-3-carboxylic acid.

Formulations

Compounds of the invention are administered to the affected tissue at the rate of from 0.1 to 200 nmole/min/kg, preferably from 1 to 50 nmol/min/kg. Such rates are easily maintained when soluble compounds are intravenously administered as discussed below. When other methods are used (e.g., oral administration), use of time-release preparations to control the rate of release of the active ingredient may be preferred. These compounds are administered in a dose of about 0.01 mg/kg/day to about 100 mg/kg/day, preferably from about 0.1 mg/kg/day to about 10 mg/kg/day.

For the purposes of this invention, the compounds of the invention may be administered by a variety of means including orally, parenterally, by inhalation spray, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophylized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 1000 μmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 0.1 to about 15 μmoles of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds of formula (I) as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the ddPN ingredient such carriers as are known in the art to be appropriate.

Formations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine kinase inhibitor compound. It will be understood, however, that the specific dose level for any particular patient will depend on a variety of factors including the activity of the specific compound employed; the age, body weight, general health, sex and diet of the individual being treated; the time and mute of administration; the rate of excretion; other drugs which have previously been administered; and the severity of the particular disease undergoing therapy, as is well understood by those skilled in the art.

Capsules comprising adenosine kinase inhibitors suitable for oral administration according to the methods of the present invention may be prepared as follows: (1) for a 10,000 capsule preparation: 1500 g of adenosine kinase inhibitor is blended with other ingredients (as described above) and filled into capsules which are suitable for administration depending on dose, from about 4 capsules per day (1 per 6 hours) to about 8 capsules per day (2 capsules per 6 hours), to an adult human.

The compounds of this invention and their preparation and use can be understood further by the representative examples above, which illustrate the various aspects of the invention without limiting its scope.

We claim:

1. A compound of the Formula

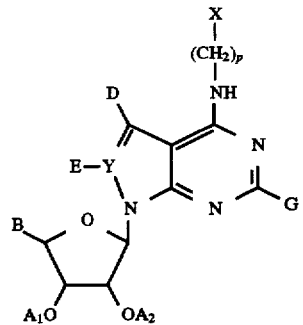

wherein:

$A_1$ and $A_2$ are each hydrogen or acyl, or together form a cyclic carbonate;

B is alkenyl, or $(CH_2)_n$—B', where n is from 1 to 4 and B' is hydrogen, hydroxy, alkyl, alkoxy, amino, azido, halogen, or alkenyl;

D is halogen, alkynyl, haloalkyl, cyano, carboxamido, or $(CH_2)_q X$, where q is 0—3;

each X is independently a carbocyclic or heterocyclic aryl, said aryl optionally substituted at any position by halogen, alkyl, alkoxy, substituted per halo lower alkyl, sulfonamide, cyano, CONRR' where R and R' are independently hydrogen or lower alkyl, or a water solubilizing group $(CH_2)_r T$, where r is from 0 to 3 and T is an alkyl chain of 1 to 16 carbons containing one or more nitrogen atoms and optionally containing one or more oxygen atoms, N-sulfonylated amino, amidoximo, N-aminoguanidino, amidino, guanidino, a cyclic amidine, a cyclic guanidine, acylated sulfonamide, a 5 or 6 membered alicyclic ring containing nitrogen and optionally containing oxygen, or the group $CONR^1R^2$, where $R^1$ and $R^2$ are independently an alkyl chain containing one or more basic nitrogen atoms, and optionally containing oxygen, or R¹ and R² together form a 5 or 6-membered ring containing at least one basic nitrogen;

Y is carbon or nitrogen;

E is nothing when Y is nitrogen, and is hydrogen or halogen when Y is carbon;

G is hydrogen or halogen;

p is from 0 to 3;

and pharmaceutically acceptable salts thereof;

provided at least one X includes a water solubilizing group as defined above.

2. A compound of claim 1, where Y is carbon.

3. A compound of claim 1, where Y is nitrogen.

4. A compound of claim 1, where D is $(CH_2)_qX$.

5. A compound of claim 1, where G and each A are hydrogen.

6. A compound of claim 2, where E, G, and each A are hydrogen.

7. A compound of claim 3, where G and each A are hydrogen.

8. A compound of claim 4, where G and each A are hydrogen.

9. A compound of claim 2, where D is $(CH_2)_qX$, and E, G and each A are hydrogen.

10. A compound of claim 4, where Y is carbon.

11. A compound of claim 4, where Y is nitrogen.

12. A compound of any one of claims 4, 10, or 11, where D includes a water solubilizing group.

13. A compound of any one of claims 4, 10, or 11, where D does not include a water solubilizing group.

14. A compound of claim 10, where D includes a water solubilizing group and A, G and E are hydrogen.

15. A compound of claim 10, where D does not include a water solubilizing group and A, G, and E are hydrogen.

16. A compound of claim 11, where D includes a water solubilizing group and A and G are hydrogen.

17. A compound of claim 11, where D does not include a water solubilizing group and A and G are hydrogen.

18. A compound of any one of claims 14–17 where each X is independently a five or six-membered ring.

19. A compound of any one of claims 14–17, where each X is independently a five or six membered ring optionally substituted at any position by halogen, alkyl, alkoxy, substituted perhaloalkyl, sulfonamide, cyano, CONRR', where R and R' are independently hydrogen or lower alkyl.

20. A compound of claim 18, where at least one T is selected from N-sulfonylated amino, amidoximo, and acylated sulfonamide.

21. A compound of claim 19, where at least one T is selected from N-sulfonylated amino, amidoximo, and acylated sulfonamide.

22. A compound of any one of claims 14–17, where X is a phenyl group.

23. A compound of any one of claims 14–17, where X is phenyl, optionally substituted at any position by halogen, alkyl, alkoxy, substituted perhaloalkyl, sulfonamide, cyano, CONRR', where R and R' are independently hydrogen or lower alkyl.

24. A compound of claim 22, where at least one T is selected from N-sulfonylated amino, amidoximo, and acylated sulfonamide.

25. A compound of claim 23, where at least one T is selected from N-sulfonylated amino, amidoximo, and acylated sulfonamide.

26. A compound of claim 10 where B is one of $CH_3$, $CH_2OH$, and $CH_2NH_2$.

27. A compound of claim 26, where B is $CH_3$.

28. A compound of claim 11 where B is one of $CH_3$, $CH_2OH$, and $CH_2NH_2$.

29. A compound of claim 28 where B is $CH_3$.

30. A compound of any of claims 4, 10 or 11, where p is 0 or 1.

31. A compound of any of claims 4, 10 or 11, where p is 0.

32. A compound of claim 1, where r is from 0 to 3 and T is one of amino, alkylamino, dialkylamino, dialkylaminoalkylamino, amidino, guanidino, cyclic amidino, an alicyclic ring containing at least one basic nitrogen, and a carboxamido containing at least one basic nitrogen.

33. A compound of claim 4, where r is from 0 to 3 and T is one of amino, alkylamino, dialkylamino, dialkylaminoalkylamino, amidino, guanidino, cyclic amidino, an alicyclic ring containing at least one basic nitrogen, and a carboxamido containing at least one basic nitrogen.

34. A compound of claim 10, where r is from 0 to 3 and T is one of amino, alkylamino, dialkylamino, dialkylaminoalkylamino, amidino, guanidino, cyclic amidino, an alicyclic ring containing at least one basic nitrogen, and a carboxamido containing at least one basic nitrogen.

35. A compound of claim 11, where r is from 0 to 3 and T is one of amino, alkylamino, dialkylamino, dialkylaminoalkylamino, amidino, guanidino, cyclic amidino, an alicyclic ring containing at least one basic nitrogen, and a carboxamido containing at least one basic nitrogen.

36. A compound of claim 4, where T is amino, alkylamino, dialkylaminoalkylamino and r is 1 to 2.

37. A compound of claim 4, where T is amidino, guanidino, amidoximo, cyclic guanidino, or cyclic amidino and r is 0 to 2.

38. A compound of claim 4, where r is 0 to 2 and T is $CONR^1R^2$ and where $R^1$ or $R^2$ are independently a chain of 2 to 16 carbons with either or both chains having at least one basic nitrogen.

39. A compound of claim 38 where $R^1$ and $R^2$ form an alicyclic ring containing a basic nitrogen.

40. A compound of claim 4, where r is 1 to 2 and T is an alicyclic ring containing 1 or more basic nitrogens and optionally containing an oxygen atom.

41. A compound of claim 4, where r is 0 to 2 and T is an acylated sulfonamide or an N-sulfonylated amine.

42. A compound of the formula where

D is phenyl, 3-pyridyl, 4-(1-morpholinomethyl)phenyl, 4-(1-piperidinoethyl)phenyl, 4-(1-piperizinoethyl)phenyl, 4-(2-aminoethyl)phenyl, 4-(N,N-dimethylaminomethyl)phenyl, 4-(N,N-diethylaminomethyl)phenyl, or 4-(N,N- diethylaminoethyl)phenyl and W is a phenyl ring containing a water solubilizing group $(CH_2)_rT$, where r is from 0 to 3 and T is amino, aminoalkyl, alkylaminoalkyl, dialkylaminoalkyl, dialkylaminalkylamino, N-sulfonylated amino, amidoximo, N-aminoguanidino, amidino, guanidino, acylated sulfonamide, or T is a 5 or 6 membered alicyclic ring, containing one or more nitrogens and optionally containing oxygen, and CONRR' where R is hydrogen or lower alkyl and R' is a carbon chain containing one or more basic nitrogens or R and R' together form an alicyclic ring containing a basic nitrogen.

43. A compound of the formula

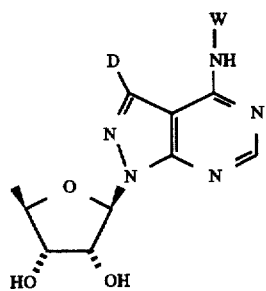

where

D is phenyl, 3-pyridyl, 4-(1-morpholinomethyl)phenyl, 4-(1-piperidinoethyl)phenyl, 4-(1-piperizinoethyl)phenyl, 4-(2-aminoethyl)phenyl, 4-(N,N-dimethylaminomethyl)phenyl, 4-(N,N-diethylaminomethyl)phenyl, or 4-(N,N-diethylaminoethyl)phenyl and W is a phenyl ring containing a water solubilizing group $(CH_2)_rT$, where r is from 0 to 3 and T is amino, aminoalkyl, alkylaminoalkyl, dialkylaminoalkyl, dialkylaminalkylamino, N-sulfonylated amino, amidoximo, N-aminoguanidino, amidino, guanidino, acylated sulfonamide, or T is a 5 or 6 membered alicyclic ring, containing one or more nitrogens and optionally containing oxygen, and CONRR' where R is hydrogen or lower alkyl and R' is a carbon chain containing one or more basic nitrogens or R and R' together form an alicyclic ring containing a basic nitrogen.

* * * * *